United States Patent
Reid et al.

(10) Patent No.: US 10,351,791 B2
(45) Date of Patent: Jul. 16, 2019

(54) QUATERNARY AMMONIUM COMPOUNDS AS FUEL OR LUBRICANT ADDITIVES

(71) Applicant: INNOSPEC LIMITED, Ellesmere Port (GB)

(72) Inventors: Jacqueline Reid, Cymau (GB); Stephen L. Cook, Chester (GB)

(73) Assignee: Innospec Limited, Cheshire (GB)

(*) Notice: Subject to any disclaimer, the term of this patent is extended or adjusted under 35 U.S.C. 154(b) by 0 days.

(21) Appl. No.: 14/907,693

(22) PCT Filed: Jul. 28, 2014

(86) PCT No.: PCT/GB2014/052311
§ 371 (c)(1),
(2) Date: Jan. 26, 2016

(87) PCT Pub. No.: WO2015/011506
PCT Pub. Date: Jan. 29, 2015

(65) Prior Publication Data
US 2016/0160142 A1 Jun. 9, 2016

(30) Foreign Application Priority Data
Jul. 26, 2013 (GB) .................................. 1313423.4

(51) Int. Cl.
*C10L 10/04* (2006.01)
*C10L 10/18* (2006.01)
(Continued)

(52) U.S. Cl.
CPC .............. *C10L 10/04* (2013.01); *C07C 57/13* (2013.01); *C07C 213/08* (2013.01);
(Continued)

(58) Field of Classification Search
CPC ........ C10L 10/04; C10L 10/18; C10L 1/2222; C10L 1/2225; C10L 1/2383; C10L 1/232;
(Continued)

(56) References Cited

U.S. PATENT DOCUMENTS 3,275,554 A 9/1966 Wagenaar
3,438,757 A 4/1969 Honnen et al.
(Continued)

FOREIGN PATENT DOCUMENTS

EP 0317846 A1 5/1989
EP 1645577 A1 4/2006
(Continued)

OTHER PUBLICATIONS

Gautier J.A. et al. Bulletin De La Societe Chimique De France, Societe Francaise De Chimie. Paris, France, Jan. 1, 1955, p. 634.
(Continued)

*Primary Examiner* — Cephia D Toomer
(74) *Attorney, Agent, or Firm* — Burns & Levinson, LLP; Janine M. Susan

(57) ABSTRACT

A quaternary ammonium compound of formula (X), wherein $R^0$, R, $R^2$ and $R^3$ is each individually an optionally substituted alkyl, alkenyl or aryl group and R includes an optionally substituted hydrocarbyl moiety having at least 5 carbon atoms.

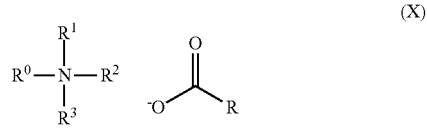

14 Claims, 1 Drawing Sheet

(51) Int. Cl.
| | |
|---|---|
| C10M 133/54 | (2006.01) |
| C10L 1/222 | (2006.01) |
| C10L 1/2383 | (2006.01) |
| C10M 133/04 | (2006.01) |
| C10M 133/08 | (2006.01) |
| C07C 213/08 | (2006.01) |
| C07C 217/28 | (2006.01) |
| C08F 110/10 | (2006.01) |
| F02M 25/00 | (2006.01) |
| C07C 57/13 | (2006.01) |
| C07D 207/408 | (2006.01) |
| C10L 1/232 | (2006.01) |
| C10M 133/44 | (2006.01) |
| F02M 25/14 | (2006.01) |

(52) U.S. Cl.
CPC ........ *C07C 217/28* (2013.01); *C07D 207/408* (2013.01); *C08F 110/10* (2013.01); *C10L 1/2222* (2013.01); *C10L 1/2225* (2013.01); *C10L 1/232* (2013.01); *C10L 1/2383* (2013.01); *C10L 10/18* (2013.01); *C10M 133/04* (2013.01); *C10M 133/08* (2013.01); *C10M 133/44* (2013.01); *C10M 133/54* (2013.01); *F02M 25/00* (2013.01); *F02M 25/14* (2013.01); *C10L 2200/0259* (2013.01); *C10L 2270/023* (2013.01); *C10L 2270/026* (2013.01); *C10M 2215/04* (2013.01); *C10M 2215/042* (2013.01); *C10M 2215/26* (2013.01); *C10N 2230/04* (2013.01); *C10N 2240/10* (2013.01); *C10N 2240/102* (2013.01); *C10N 2240/104* (2013.01)

(58) Field of Classification Search
CPC ....... C10L 2200/0259; C10L 2270/026; C10L 2270/023; C10M 133/54; C10M 133/04; C10M 133/08; C10M 133/44; C10M 2215/04; C10M 2215/042; C10M 2215/26; C07C 213/08; C07C 217/28; C07C 57/13; F02M 25/00; F02M 25/14; C10N 2230/04; C10N 2240/10; C10N 2240/102; C10N 2240/104; C08F 110/10; C07D 207/408

See application file for complete search history.

(56) References Cited

U.S. PATENT DOCUMENTS

| | | |
|---|---|---|
| 3,454,555 A | 7/1969 | van der Voort et al. |
| 3,565,804 A | 2/1971 | Honnen et al. |
| 3,755,433 A | 8/1973 | Miller et al. |
| 3,822,209 A | 7/1974 | Knapp et al. |
| 4,071,327 A | 1/1978 | Dorer, Jr. |
| 4,171,959 A | 10/1979 | Vartanian et al. |
| 4,248,719 A | 2/1981 | Chafetz et al. |
| 4,288,612 A | 9/1981 | Lewis et al. |
| 4,715,976 A | 12/1987 | Mori et al. |
| 5,089,029 A | 2/1992 | Hashimoto et al. |
| 5,112,364 A | 5/1992 | Rath et al. |
| 5,567,716 A | 10/1996 | Della Valle et al. |
| 5,588,973 A | 12/1996 | Blackborow et al. |
| 5,925,151 A | 7/1999 | DeCanio et al. |
| 6,143,038 A | 11/2000 | Yamamoto et al. |
| 6,217,624 B1 | 4/2001 | Morris et al. |
| 6,967,258 B2 | 11/2005 | Kanbara et al. |
| 7,951,211 B2 | 5/2011 | Barton et al. |
| 2008/0052985 A1 | 3/2008 | Stevenson et al. |
| 2008/0060259 A1 | 3/2008 | Breakspear et al. |
| 2008/0060608 A1 | 3/2008 | Breakspear et al. |
| 2008/0113890 A1 | 5/2008 | Moreton et al. |
| 2008/0307698 A1 | 12/2008 | Barton et al. |
| 2009/0282731 A1 | 11/2009 | Malfer et al. |
| 2010/0191014 A1 | 7/2010 | Iwase et al. |
| 2011/0258917 A1 | 10/2011 | Garcia Castro et al. |
| 2011/0315107 A1 | 12/2011 | Grabarse et al. |
| 2012/0010112 A1 | 1/2012 | Grabarse et al. |
| 2012/0138004 A1 | 6/2012 | Stevenson et al. |
| 2012/0285482 A1 | 11/2012 | Beck |
| 2013/0031827 A1 | 2/2013 | Reid et al. |
| 2013/0118062 A1* | 5/2013 | Fang .................... C10L 1/2222 44/405 |
| 2014/0123547 A1 | 5/2014 | Walter |
| 2014/0174390 A1 | 6/2014 | Reid et al. |
| 2015/0034036 A1 | 2/2015 | Burgess et al. |
| 2016/0130514 A1 | 5/2016 | Hansch et al. |

FOREIGN PATENT DOCUMENTS

| | | |
|---|---|---|
| EP | 1884556 A2 | 2/2008 |
| EP | 1900795 A1 | 3/2008 |
| EP | 2589647 A1 | 4/2011 |
| EP | 2604674 A1 | 12/2011 |
| EP | 3004294 B1 | 4/2017 |
| FR | 2249948 A1 | 5/1975 |
| GB | 2496514 A | 5/2013 |
| GB | 2521022 A | 10/2015 |
| JP | 11217771 A | 8/1999 |
| JP | 2005048000 A | 2/2005 |
| JP | 2006199939 A | 8/2006 |
| WO | 02094889 A2 | 11/2002 |
| WO | 2006135881 A2 | 12/2006 |
| WO | 2007044693 A2 | 4/2007 |
| WO | 2007071415 A1 | 6/2007 |
| WO | 2008027881 A2 | 3/2008 |
| WO | 2009040583 A1 | 4/2009 |
| WO | 2010132259 A1 | 11/2010 |
| WO | 2011149799 A1 | 1/2011 |
| WO | 2011095819 A1 | 8/2011 |
| WO | 2012177277 A1 | 12/2012 |
| WO | 2013017884 A1 | 2/2013 |
| WO | 2013043332 A1 | 3/2013 |
| WO | 2014064151 A1 | 5/2014 |
| WO | 2010132359 A1 | 9/2014 |

OTHER PUBLICATIONS

Yu, Y. et al. Biodegradable Naphthenic Acid Ionic Liquids: Synthesis, Characterization, and Quantitative Structure-Biodegradation Relationship, Chemistry—A European Journal, vol. 14, No. 35, Dec. 8, 2008, pp. 11174-11182.

Petkovic, M. et al. Novel biocompatible cholinium-based ionic liquids-toxicity and biodegradability, Green Chemistry, vol. 12, No. 4, Jan. 1, 2010, p. 643.

Li, Z. et al. Design of environmentally friendly ionic liquid aqueous two-phase systems for the efficient and high activity extraction of proteins, Green Chemistry, vol. 14, No. 10, Jan. 1, 2012, p. 2941.

Lopatin, B.V. et al. Utilization of the IR and UV spectra to determine the authenticity of antihelminthic preparations—Derivatives of quaternary ammonium salts. Pharmaceutical Chemistry Journal, Jul. 1, 1983, pp. 865-868.

International Search Report and Written Opinion for PCT/GB2014/052311 dated Oct. 21, 2014.

Great Britain Search Report for GB1313423 dated Jan. 27, 2014.

International Preliminary Report on Patentability for PCT/GB2014/052311 dated Feb. 4, 2016.

Ronald Breslow et al., Journal of the American Chemical Society, vol. 103, 1981, R. Breslow et al., "Selective Functionalization of Doubly Coordinated Flexible Chains", pp. 2905-2907.

Jens Norrman et al., Journal of Physical Chemistry B, vol. 111, 2007, "Phase Behavior of Cetyltrimethylammonium Surfactants with Oligo Carboxylate Counterions Mixed with Water and Decanol: Attraction between Charged Planes or Spheres with Oligomeric Counterions", pp. 13364-13370.

Yong-Chan Chung et al., Langmuir, vol. 9, 1993 American Chemical Society, "Counterion Control over the Barrier Properties of Bilayers Derived from Double-Chain Ionic Surfactants", pp. 1937-1939.

(56) References Cited

OTHER PUBLICATIONS

Patents Act 1977: Search Report under Section 17, International Application No. GB1606011.3 (2 pgs.).
Patents Act 1977: Search Report under Section 17, International Application No. GB1517426.1 (2 pgs.).
Patents Act 1977: Search Report under Section 17, International Application No. GB1413353.2 (2 pgs.).
Patents Act 1977: Search Report under Section 17, International Application No. GB1413354.0 (2 pgs.).
European Office Action dated Apr. 12, 2017 for Application No. 14 744 947.4, pp. 1-5.

* cited by examiner

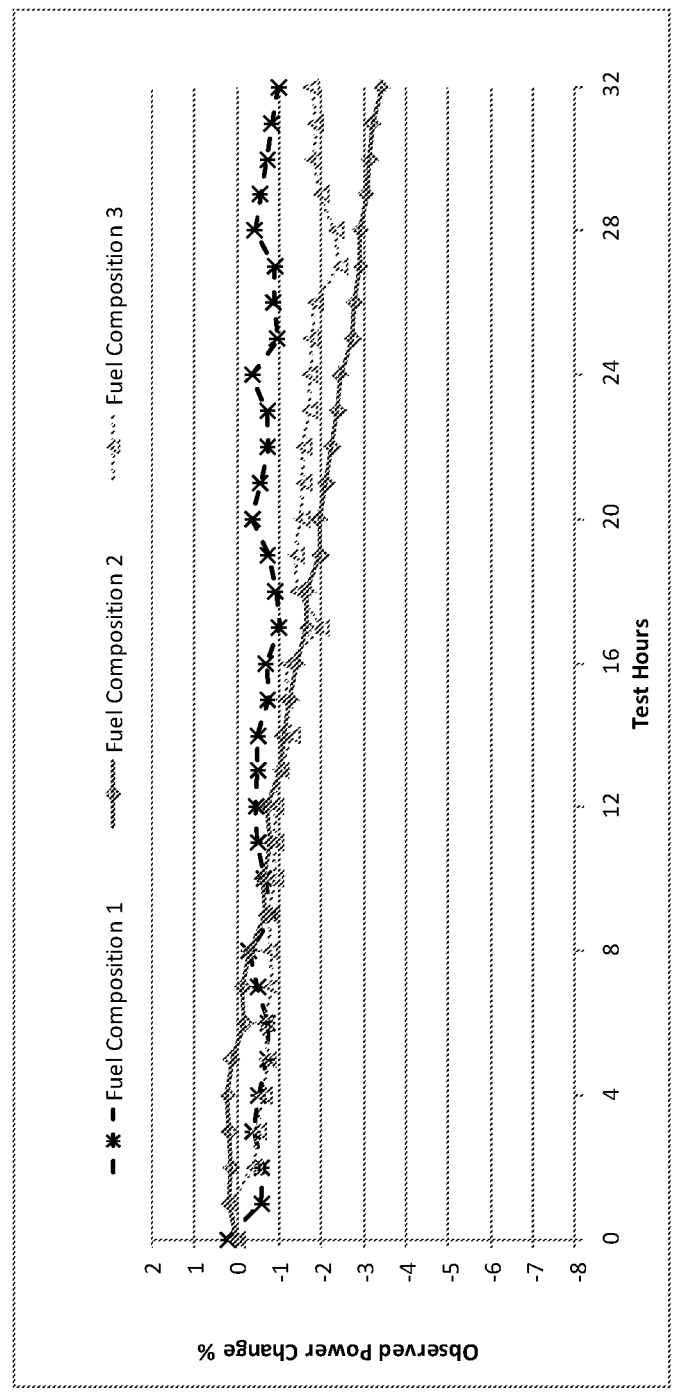

QUATERNARY AMMONIUM COMPOUNDS AS FUEL OR LUBRICANT ADDITIVES

CROSS-REFERENCE TO RELATED APPLICATIONS

This application is a U.S. national stage application under 35 U.S.C. 371 of co-pending International Application No. PCT/GB2014/052311 filed on Jul. 28, 2014 and entitled QUATERNARY AMMONIUM COMPOUNDS AS FUEL OR LUBRICANT ADDITIVES, which in turn claims priority to Great Britain Patent Application No. 1313423.4, filed on Jul. 26, 2013, the contents of which are incorporated by reference herein in their entirety for all purposes.

The present invention relates to novel quaternary ammonium compounds, to compositions comprising such compounds and to methods and uses relating thereto.

In particular the present invention relates to the use of quaternary ammonium compounds as fuel or lubricant additives, especially as fuel additives, for example diesel fuel additives or gasoline fuel additives.

It is common to include nitrogen-containing detergent compounds in lubricating oil and fuel oil compositions in order to improve the performance of engines using such compositions. The inclusion of detergent additives prevents the fouling of moving parts of the engine. Without such additives fouling would cause the performance of the engine to diminish and eventually cease.

Many different types of quaternary ammonium salts are known in the art for use as detergent additives in fuel and lubricating oil compositions. Examples of such compounds are described in U.S. Pat. No. 4,171,959 and U.S. Pat. No. 7,951,211. One commonly used class of quaternary ammonium additives is prepared by the reaction of a tertiary amine with an epoxide and an acid. Various acids may be used but typically these are small acid molecules, for example acetic acid, and the counterion to the quaternary ammonium cation is not considered to be of importance.

Detergent additive compounds typically include a polar group and a hydrophobic group. The hydrophobic group is typically a long chain hydrocarbyl moiety. A common feature of existing quaternary ammonium salt detergent additives is that the hydrophobic group is included within the cationic portion of the compound. The present inventors have surprisingly found that quaternary ammonium salts including a hydrophobic moiety in the anion can provide good performance as a detergent.

According to a first aspect of the present invention there is provided a quaternary ammonium compound of formula (X):

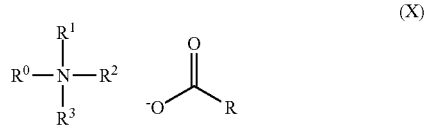

(X)

wherein $R^0$, $R^1$, $R^2$ and $R^3$ is each individually an optionally substituted alkyl, alkenyl or aryl group and R includes an optionally substituted hydrocarbyl moiety having at least 5 carbon atoms.

In this specification, unless otherwise stated references to optionally substituted alkyl groups may include aryl-substituted alkyl groups and references to optionally-substituted aryl groups may include alkyl-substituted or alkenyl-substituted aryl groups.

R includes an optionally substituted hydrocarbyl moiety having at least 5 carbon atoms. Preferably R includes an optionally substituted hydrocarbyl moiety having at least 6 carbon atoms. Preferably R includes an optionally substituted alkyl or alkenyl moiety having at least 6 carbon atoms. R is preferably an optionally substituted alkyl, alkenyl or aryl group which includes an optionally substituted alkyl or alkenyl moiety having at least 5 carbon atoms. For example R may include a phenyl ring but it preferably further includes an alkyl or alkenyl chain of at least 5 carbon atoms. Thus R may be an alkyl-substituted aryl group.

The quaternary ammonium salt of the present invention may be prepared by any suitable means. Suitable methods will be known to the person skilled in the art.

In one embodiment, $R^0$ is an alkyl group and the quaternary ammonium compound is prepared from an ester of formula $RCOOR^0$. In such embodiments $R^0$ is preferably methyl.

In preferred embodiments the quaternary ammonium compound is prepared from a tertiary amine, an alkylating agent and an acid. Thus $R^0$ is preferably the residue of an alkylating agent.

In a preferred embodiment the first aspect of the present invention provides a quaternary ammonium compound which is the reaction product of:
(a) a tertiary amine;
(b) an acid-activated alkylating agent; and
(c) an acid including an optionally substituted hydrocarbyl moiety having at least 5 carbon atoms.

According to a second aspect of the present invention there is provided a method of preparing a quaternary ammonium salt, the method comprising reacting (a) a tertiary amine with (b) an acid-derived alkylating agent in the presence of (c) an acid including an optionally substituted hydrocarbyl moiety having at least 5 carbon atoms.

Preferably component (c) is an acid including an optionally substituted hydrocarbyl moiety having at least 6 carbon atoms.

Further preferred features of the first and second aspects of the invention will now be defined.

Component (a) used to prepare the quaternary ammonium salts of the present invention is a tertiary amine. Any suitable tertiary amine may be used.

In some embodiments of the present invention the tertiary amine may be a small compound of low complexity and low molecular weight. In some embodiments the tertiary amine may be a complex molecule and/or a molecule of high molecular weight which includes a tertiary amine group.

The tertiary amine compounds of the present invention preferably do not include any primary or secondary amine groups. In some embodiments they may be derived from compounds including these groups but preferably these have been subsequently reacted to form additional tertiary amine species. The tertiary amine compound used as component (a) may contain more than one tertiary amine group. However tertiary amine compounds including primary or secondary amine groups are within the scope of the invention provided these groups do not prevent quaternisation of the tertiary amine species.

Tertiary amines for use herein are preferably compounds of formula $R^1R^2R^3N$, wherein each of $R^1$, $R^2$ and $R^3$ is independently an optionally substituted alkyl, alkenyl or aryl group.

$R^1$, $R^2$ and $R^3$ may be the same or different. In some preferred embodiments $R^1$ and $R^2$ are the same and $R^3$ is different.

Preferably each of $R^1$ and $R^2$ is independently an optionally substituted alkyl, alkenyl or aryl group having from 1 to 50 carbon atoms, preferably from 1 to 40 carbon atoms, more preferably from 1 to 30 carbon atoms.

Each of $R^1$ and $R^2$ may be optionally substituted with one or more groups selected from halo (especially chloro and fluoro), hydroxy, alkoxy, keto, acyl, cyano, mercapto, alkylmercapto, dialkylamino, nitro, nitroso, and sulphoxy. The alkyl groups of these substituents may be further substituted.

Preferably each of $R^1$ and $R^2$ is independently an optionally substituted alkyl or alkenyl group. Preferably each of $R^1$ and $R^2$ is independently an optionally substituted alkyl group. Preferably each of $R^1$ and $R^2$ is independently an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms.

Preferably $R^1$ is an optionally substituted alkyl or alkenyl group, preferably having from 1 to 10, preferably from 1 to 4 carbon atoms. Preferably $R^1$ is an alkyl group. It may be a substituted alkyl group, for example a hydroxy substituted alkyl group. Preferably $R^1$ is an unsubstituted alkyl group. The alkyl chain may be straight-chained or branched. Preferably $R^1$ is selected from methyl, ethyl, propyl and butyl, including isomers thereof. Most preferably $R^1$ is methyl.

Preferably $R^2$ is an optionally substituted alkyl or alkenyl group, preferably having from 1 to 10, preferably from 1 to 4 carbon atoms. Preferably $R^2$ is an alkyl group. It may be a substituted alkyl group, for example a hydroxy substituted alkyl group. Preferably $R^2$ is an unsubstituted alkyl group. The alkyl chain may be straight-chained or branched. Preferably $R^2$ is selected from methyl, ethyl, propyl and butyl, including isomers thereof. Most preferably $R^2$ is methyl.

In some embodiments $R^3$ is an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms. Suitable substituents include halo (especially chloro and fluoro), hydroxy, alkoxy, keto, acyl, cyano, mercapto, alkylmercapto, amino, alkylamino, nitro, nitroso, sulphoxy, amido, alkyamido, imido and alkylimido. The alkyl groups of these substituents may be further substituted.

In some embodiments $R^3$ is an optionally substituted alkyl or alkenyl group, preferably having from 1 to 10, preferably from 1 to 4 carbon atoms. Suitably $R^3$ is an optionally substituted alkyl group. Preferably $R^3$ is a substituted alkyl group. Preferred substituents include alkoxy and hydroxyl groups.

In some preferred embodiments $R^3$ is a hydroxyl-substituted alkyl group. The alkyl chain may be straight-chained or branched. Most preferably $R^3$ is a hydroxyethyl group.

In some embodiments $R^3$ is an optionally substituted hydrocarbyl group, for example an optionally substituted hydrocarbyl group having from 1 to 300 carbon atoms, for example from 1 to 200 carbon atoms. $R^3$ may be an optionally substituted hydrocarbyl group having a number average molecular weight of from 100 to 5000, preferably from 500 to 2500.

As used herein, the term "hydrocarbyl" substituent or group is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon groups, that is, substituents containing non-hydrocarbon groups (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

In some embodiments $R^3$ is an optionally substituted alkyl or alkenyl group. $R^3$ may be an unsubstituted alkyl or alkenyl group. Suitably $R^3$ is an alkyl or alkenyl group having from 1 to 200 carbon atoms.

Suitably $R^3$ is a polyisobutenyl group, preferably a polyisobutenyl group having a molecular weight of from 100 to 5000, preferably from 300 to 4000, suitably from 450 to 2500, for example from 500 to 2000 or from 600 to 1500.

In some embodiments $R^3$ is an optionally substituted alkylene phenol moiety and the tertiary amine $R^1R^2R^3$ is s the product of a Mannich reaction between an aldehyde, an optionally substituted phenol and an amine. Suitably the aldehyde is formaldehyde. The amine used to prepare the Mannich compound may be a monoamine and $R^3$ would have the structure (A):

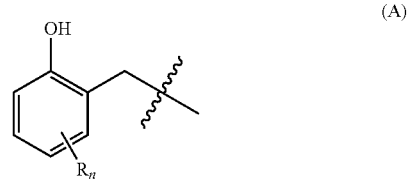

(A)

The amine used to prepare the Mannich compound may be a polyamine, including at least one tertiary amine group and $R^3$ may have the structure (B):

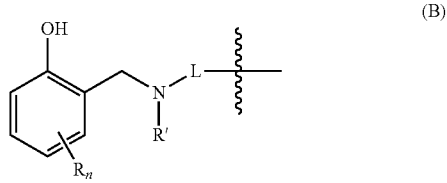

(B)

In structures (A) and (B) n is 0 to 4, preferably 1, R is an optionally substituted hydrocarbyl group, R' is an optionally substituted alkyl, alkenyl or aryl group; and L is a linking group.

R' and L may together form a heterocyclic group.

R' is preferably an alkyl group, preferably an unsubstituted alkyl group. R' is suitably a $C_1$ to $C_4$ alkyl group.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

In some preferred embodiments, the phenol includes an ortho-methyl substituent and a further substituent R at the para-position.

In a preferred embodiment, n is 1 and the optionally substituted hydrocarbyl substituent R is preferably para to the hydroxyl group.

The optionally substituted hydrocarbyl substituent R of the phenol can have 6 to 400 carbon atoms, suitably 30 to 180 carbon atoms, for example 10 or 40 to 110 carbon atoms. This hydrocarbyl substituent can be derived from an olefin or a polyolefin.

The polyolefins which can form the hydrocarbyl substituent can be prepared by polymerizing olefin monomers by well known polymerization methods and are also commercially available.

Some preferred polyolefins include polyisobutylenes having a number average molecular weight of 200 to 3000, in another instance of 400 to 2500, and in a further instance of 400 or 500 to 1500.

In some embodiments the phenol may include a lower molecular weight alkyl substituent for example a phenol which carries one or more alkyl chains having a total of less than 28 carbon atoms, preferably less than 20 carbon atoms, more preferably less than 14 carbon atoms.

A monoalkyl phenol may be preferred, suitably having from 4 to 20 carbons atoms, preferably 8 to 16 carbon atoms, for example a phenol having a $C_{12}$ alkyl substituent.

In some embodiments $R^3$ may include an ether, amide or ester group.

In some embodiments $R^3$ includes succinimide moiety. $R^3$ may have the formula:

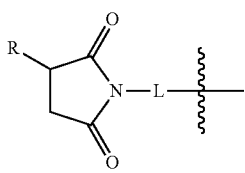

wherein R is an optionally substituted hydrocarbyl group and L is a linking group.

In some embodiments the optionally substituted hydrocarbyl substituent R can have 6 to 36 carbon atoms, preferably 8 to 22, for example 10 to 18 or 16 to 18 carbon atoms.

In some embodiments the optionally substituted hydrocarbyl substituent R can have 6 to 400 carbon atoms, suitably 30 to 180 carbon atoms, for example 10 or 40 to 110 carbon atoms. This hydrocarbyl substituent can be derived from an olefin or a polyolefin.

Some preferred polyolefins include polyisobutylenes having a number average molecular weight of 200 to 3000, in another instance of 400 to 2500, and in a further instance of 400 or 500 to 1500.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

$R^3$ may suitably be selected from an optionally substituted alkyl or alkenyl group having 1 to 10 carbon atoms; an optionally substituted hydrocarbyl group having a molecular weight of 100 to 5000; an optionally substituted alkylene phenol moiety and an optionally substituted alkylene succinimide group.

Suitable tertiary amine compounds for use as component (a) include simple alkylamino and hydroxyalkylamino compounds; trialkylamino compounds having a high molecular weight substituent; Mannich reaction products including a tertiary amine and substituted acylated amines or alcohols including a tertiary amine.

Simple alkylamino and hydroxyalkyl amino compounds are preferably compounds of formula $R^1R^2R^3N$, wherein each of $R^1$, $R^2$ and $R^3$ is an alkyl group or a hydroxyalkyl group. Each of $R^1$, $R^2$ and $R^3$ may be the same or different. Suitably each of $R^1$, $R^2$ and $R^3$ is independently selected from an alkyl or hydroxyalkyl group having 1 to 10, preferably 1 to 6 carbon atoms, for example 1 to 4 carbon atoms. Each of $R^1$, $R^2$ and $R^3$ may be independently selected from methyl, ethyl, propyl, butyl, pentyl, hexyl, hydroxymethyl, hydroxyethyl, hydroxypropyl, hydroxybutyl, hydroxypentyl and hydroxyhexyl. Component (a) may be a trialkylamine, a dialkylhydroxyalkylamine, a dihydroxyalkylalkylamine or a trihydroxyalkylamine. There are many different compounds of this type and these will be known to the person skilled in the art.

Trialkylamino compounds having a high molecular weight substituent suitable for use herein are typically polyalkene-substituted amines including at least one tertiary amino group.

The polyalkene-substituted amines having at least one tertiary amino group of the present invention may be derived from an olefin polymer and an amine, for example ammonia, monoamines, polyamines or mixtures thereof. They may be prepared by a variety of methods such as those described and referred to in US 2008/0113890.

Suitably the polyalkene substituent of the polyalkene-substituted amine is derived from a polyisobutylene.

The amines that can be used to make the polyalkene-substituted amine include ammonia, monoamines, polyamines, or mixtures thereof, including mixtures of different monoamines, mixtures of different polyamines, and mixtures of monoamines and polyamines (which include diamines). The amines include aliphatic, aromatic, heterocyclic and carbocyclic amines. Preferred amines are generally substituted with at least one hydrocarbyl group having 1 to about 50 carbon atoms, preferably 1 to 30 carbon atoms. Saturated aliphatic hydrocarbon radicals are particularly preferred.

The monoamines and polyamines suitably include at least one primary or secondary amine group.

The number average molecular weight of the polyalkene-substituted amines can range from 500 to 5000, or from 500 to 3000, for example from 1000 to 1500.

Any of the above polyalkene-substituted amines which are secondary or primary amines, may be alkylated to tertiary amines using alkylating agents. Suitable alkylating agents and methods using these will be known to the person skilled in the art.

Suitable Mannich reaction products having a tertiary amine for use as component (a) are described in US 2008/0052985.

The Mannich reaction product having a tertiary amine group is prepared from the reaction of an optionally substituted hydrocarbyl-substituted phenol, an aldehyde and an amine. The optionally substituted hydrocarbyl-substituted phenol is suitably as previously described herein Preferably the optionally substituted hydrocarbyl-substituted phenol is a polyisobutenyl-substituted phenol or a polyisobutenyl-substituted cresol.

The aldehyde used to form the Mannich detergent can have 1 to 10 carbon atoms, and is generally formaldehyde or a reactive equivalent thereof such as formalin or paraformaldehyde.

The amine used to form the Mannich detergent can be a monoamine or a polyamine.

Examples of monoamines and polyamines are known to the person skilled in the art.

Preferred polyamines are polyethylene polyamines.

In especially preferred embodiments the amine used to form the Mannich detergent comprises a diamine. Suitably it includes a primary or secondary amine which takes part in the Mannich reaction and in addition a tertiary amine.

One preferred amine is dimethylaminopropylamine.

In preferred embodiments the Mannich detergent is the product directly obtained from a Mannich reaction and comprising a tertiary amine. For example the amine may comprise a single primary or secondary amine which when reacted in the Mannich reaction forms a tertiary amine which is capable of being quaternised. Alternatively the amine may comprise a primary or secondary amine capable of taking part in the Mannich reaction and also a tertiary amine capable of being quaternised. However the Mannich detergent may comprise a compound which has been obtained from a Mannich reaction and subsequently reacted to form a tertiary amine, for example a Mannich reaction may yield a secondary amine which is then alkylated to form a tertiary amine.

Suitable preferred amines include dimethylamine and dibutylamine.

Substituted acylated amines or alcohols including a tertiary amine for use as component (a) include the reaction product of an optionally substituted hydrocarbyl-substituted acylating agent and a compound having an oxygen or nitrogen atom capable of condensing with said acylating agent and further having a tertiary amino group.

The optionally substituted hydrocarbyl substituted acylating agent is preferably a mono- or polycarboxylic acid (or reactive equivalent thereof) for example a substituted succinic, phthalic or propionic acid.

Preferred hydrocarbyl substituted acylating agents for use in the preparation of component (i) are polyisobutenyl substituted succinic acid derivatives. Preferred compounds are those having a polyisobutenyl group with a molecular weight of from 100 to 5000, preferably from 300 to 4000, suitably from 450 to 2500, for example from 500 to 2000 or from 600 to 1500.

In some preferred embodiments the tertiary amine comprises a compound formed by the reaction of an optionally substituted hydrocarbyl-substituted acylating agent and an amine of formula (I) or (II):

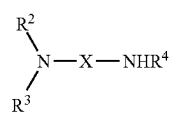

(I)

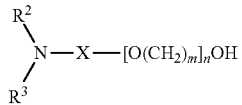

(II)

wherein $R^2$ and $R^3$ are the same or different alkyl, alkenyl or aryl groups having from 1 to 22 carbon atoms; X is a bond or is an alkylene group having from 1 to 20 carbon atoms; n is from 0 to 20; m is from 1 to 5; and $R^4$ is hydrogen or a $C_1$ to $C_{22}$ alkyl group.

The conditions of the above reaction are suitably selected to ensure that there are no free acid groups present in the tertiary amine component (a) that is formed. For example when a compound of formula (I) is reacted with a succinic acid derived acylating agent the reaction conditions or ratio of reactants are selected to ensure that the imide or diamide are formed. The monoamide is not formed. When a compound of formula (II) is reacted with a succinic acid derived acylating agent the reaction conditions or ratio of reactants are selected to ensure that the diester is formed. The monoester is not formed.

When a compound of formula (I) is used, $R^4$ is preferably hydrogen or a $C_1$ to $C_{18}$, suitably a $C_1$ to $C_{16}$ alkyl group. More preferably $R^4$ is selected from hydrogen, methyl, ethyl, propyl, butyl and isomers thereof. Most preferably $R^4$ is hydrogen.

When a compound of formula (II) is used, m is preferably 2 or 3, most preferably 2; n is preferably from 0 to 15, preferably 0 to 10, more preferably from 0 to 5. Most preferably n is 0 and the compound of formula (II) is an alcohol.

Preferably the optionally substituted hydrocarbyl substituted acylating agent is reacted with a diamine compound of formula (I).

$R^2$ and $R^3$ are the same or different alkyl, alkenyl or aryl groups having from 1 to 22 carbon atoms. In some embodiments $R^2$ and $R^3$ may be joined together to form a ring structure, for example a piperidine, imidazole or morpholine moiety. Thus $R^2$ and $R^3$ may together form an aromatic and/or heterocyclic moiety. $R^2$ and $R^3$ may be branched alkyl or alkenyl groups. Each may be substituted, for example with a hydroxy or alkoxy substituent.

Preferably each of $R^2$ and $R^3$ is independently a $C_1$ to $C_{16}$ alkyl group, preferably a $C_1$ to $C_{10}$ alkyl group. $R^2$ and $R^3$ may independently be methyl, ethyl, propyl, butyl, pentyl, hexyl, heptyl, octyl, or an isomer of any of these. Preferably $R^2$ and $R^3$ is each independently $C_1$ to $C_4$ alkyl. Preferably $R^2$ is methyl. Preferably $R^3$ is methyl.

X is a bond or alkylene group having from 1 to 20 carbon atoms. X is preferably an alkylene group having 1 to 12 carbon atoms, more preferably 1 to 8 carbon atoms, for example 2 to 6 carbon atoms or 2 to 5 carbon atoms. Most preferably X is an ethylene, propylene or butylene group, especially a propylene group.

Examples of compounds of formula (I) suitable for use herein will be known to the person skilled in the art.

In some preferred embodiments the compound of formula (I) is selected from N,N-dimethyl-1,3-diaminopropane, N,N-diethyl-1,3-diaminopropane, N,N-dimethylethylenediamine, N,N-diethylethylenediamine, N,N-dibutylethylenediamine, or combinations thereof.

Examples of compounds of formula (II) suitable for use herein will be known to the person skilled in the art.

In some preferred embodiments the compound of formula (II) is selected from Triisopropanolamine, 1-[2-hydroxyethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethylaminoethanol, 2-dimethylamino-2-methyl-1-propanol, or combinations thereof.

An especially preferred compound of formula (I) is N,N-dimethyl-1,3-diaminopropane (dimethylaminopropylamine).

Further especially preferred tertiary amine compounds (a) are formed by the reaction of a compound including a primary amine group and a tertiary amine group and a polyisobutenyl-substituted succinic acid. One especially preferred amine compound having a primary and a tertiary amine group is dimethylaminopropylamine. The polyisobutenyl substituent preferably has a molecular weight of from 300 to 2500, suitably from 500 to 1500. Thus an especially preferred compound for use as component (a) is a polyisobutenyl-substituted succinimide prepared from dimethylaminopropylamine.

Especially preferred tertiary amine compounds for use as component (a) include N,N-dimethyl ethanolamine, dimethyloctadecylamine and N-methyl N-N-ditallowamine.

Component (b) used to prepare the quaternary ammonium compound of the present invention in preferred embodiments is an acid activated alkylating agent. Preferred acid-activated alkylating agents are epoxide compounds.

Any suitable epoxide compound may be used. Suitable epoxide compounds are those of formula:

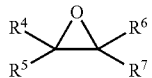

wherein each of $R^4$, $R^5$, $R^6$, $R^7$ is independently selected from hydrogen or an optionally substituted alkyl, alkenyl or aryl group.

In such embodiments $R^0$ as shown in formula (X) is thus suitably a group of formula:

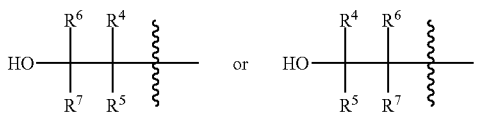

At least one of $R^4$, $R^5$, $R^6$ and $R^7$ is hydrogen. Preferably at least two of $R^4$, $R^5$, $R^6$ and $R^7$ are hydrogen. Most preferably three of $R^4$, $R^5$, $R^6$ and $R^7$ are hydrogen. $R^4$, $R^5$, $R^6$ and $R^7$ may be all hydrogen.

In the structure above and the definitions which follow $R^4$ and $R^5$ are interchangeable and thus when these groups are different either enantiomer or diastereomer may be used as component (b).

In the structure above and the definitions which follow $R^6$ and $R^7$ are interchangeable and thus when these groups are different either enantiomer or diastereomer may be used as component (b).

Preferably $R^4$ is hydrogen or an optionally substituted alkyl, alkenyl or aryl group, preferably having from 1 to 10, preferably from 1 to 4 carbon atoms. Preferably $R^4$ is hydrogen or an alkyl group. Most preferably $R^4$ is hydrogen.

Preferably $R^5$ is hydrogen or an optionally substituted alkyl, alkenyl or aryl group, preferably having from 1 to 10 carbon atoms. For example $R^5$ may be benzyl.

In some preferred embodiments $R^5$ is an optionally substituted aryl group. For example $R^5$ may be phenyl.

In some preferred embodiments $R^5$ is an optionally substituted alkyl or alkenyl group. Suitably $R^5$ is an alkyl group, for example an unsubstituted alkyl group. $R^5$ may be an alkyl group having 1 to 12, for example 1 to 8 or 1 to 4 carbon atoms.

Preferably $R^5$ is hydrogen or an alkyl group. Most preferably $R^5$ is hydrogen.

Preferably $R^6$ is hydrogen or an optionally substituted alkyl, alkenyl or aryl group, preferably having from 1 to 10, preferably from 1 to 4 carbon atoms. Preferably $R^6$ is hydrogen or an alkyl group. Most preferably $R^6$ is hydrogen.

Preferably $R^7$ is hydrogen or an optionally substituted alkyl, alkenyl or aryl group.

In some preferred embodiments $R^7$ is an optionally substituted aryl group. For example $R^7$ may be phenyl.

In some preferred embodiments $R^7$ is an optionally substituted alkyl or alkenyl group. $R^7$ may be an alkyl group, for example an unsubstituted alkyl group. $R^7$ may be an alkyl group having 1 to 50 carbon atoms, preferably from 1 to 30 carbon atoms, suitably 1 to 20 carbon atoms, preferably from 1 to 12 carbon atoms, for example from 1 to 8 or from 1 to 4 carbon atoms.

In some embodiments $R^7$ is hydrogen.

In some preferred embodiments $R^7$ is the moiety $CH_2OR^8$ or $CH_2OCOR^9$ wherein each of $R^8$ and $R^9$ may be an optionally substituted alkyl, alkenyl or aryl group.

$R^8$ is preferably an optionally substituted alkyl or aryl group, preferably having from 1 to 30 carbon atoms, preferably from 1 to 20 carbon atoms, suitably from 1 to 12 carbon atoms.

When $R^8$ is an alkyl group it may be straight-chained or branched. In some embodiments it is branched. $R^8$ may be an optionally substituted phenyl group.

In one embodiment $R^8$ is a 2-methyl phenyl group. In another embodiment $R^8$ is $CH_2C(CH_2CH_3)CH_2CH_2CH_3$.

$R^9$ may be an optionally substituted alkyl, alkenyl or aryl group.

$R^9$ is preferably an optionally substituted alkyl or aryl group, preferably having from 1 to 30 carbon atoms, preferably from 1 to 20 carbon atoms, suitably from 1 to 12 carbon atoms. When $R^9$ is an alkyl group it may be straight-chained or branched. In some preferred embodiments it is branched. $R^9$ may be an optionally substituted phenyl group.

In one embodiment $R^9$ is $C(CH_3)R_2$ wherein each R is an alkyl group. The R groups may be the same or different.

Component (b) is preferably an epoxide. The present invention therefore provides a quaternary ammonium compound which is the reaction product of:
(a) a tertiary amine;
(b) an epoxide; and
(c) an acid including an optionally substituted alkyl or alkenyl moiety having at least 5 carbon atoms, preferably at least 6 carbon atoms.

Preferred epoxide compounds for use as component (b) include styrene oxide, ethylene oxide, propylene oxide, butylene oxide, epoxyhexane, octene oxide, stilbene oxide and other alkyl and alkenyl epoxides having 2 to 50 carbon atoms.

Other suitable epoxide compounds include glycidyl ethers and glycidyl esters, for example gylcidyl 2 methyl phenyl ether and glycidyl ester of versatic acid.

Component (c) used to prepare the quaternary ammonium salts of the present invention is an acid including an optionally substituted hydrocarbyl moiety having at least 5 carbon atoms, preferably at least 6 carbon atoms. The optionally substituted hydrocarbyl moiety is as described above.

Component (c) includes at least one acid functional group and at least one optionally substituted hydrocarbyl moiety having at least 5 carbon atoms, preferably at least 6 carbon atoms. In some embodiments component (c) may be a simple fatty acid compound. However component (c) may also be a more complex molecule including these functional groups.

For the avoidance of doubt component (c) is an acid which activates the alkylating agent (b) and forms the anionic counterion of the quaternary ammonium salt.

Component (c) is a separate component to component (a). The quaternary ammonium salts of the present invention are prepared from the reaction of three separate molecules.

The quaternary ammonium compounds of the present invention are different to the compounds described by Lubrizol in US2012/0138004 in which the molecule containing the tertiary amine group provides a proton to activate the epoxide alkylating agent.

Component (c) is preferably an acid including an optionally substituted hydrocarbyl moiety having at least 6 carbon atoms, suitably at least 8 carbons, preferably at least 10 carbons, for example at least 12 carbon atoms.

Component (c) is suitably an acid of formula RCOOH. R may comprise one or more additional acid or ester groups. It may be a monoacid, a diacid or a polyacid. It may be a monoester of a diacid or a partial ester of a polyacid. Thus R may be —R'H, —R'COOH, —R'COOR", R'(COOR")$_n$ wherein each R' is independently an optionally substituted hydrocarbyl group, each R" may independently be H or an optionally substituted hydrocarbyl group and n is at least 1.

In some embodiments component (c) is a monoacid and R is an optionally substituted $C_6$ to $C_{50}$ alkyl or alkenyl group, preferably a $C_5$ to $C_{40}$ alkyl or alkenyl group, for example a $C_{10}$ to $C_{36}$ or a $C_{12}$ to $C_{30}$ alkyl or alkenyl group.

Suitable monoacids for use as component (c) include caprylic acid, capris acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, arachidonic acid, eicosapentaenoic acid, erucic acid, undecylenic acid and docosahexenoic acid.

In some preferred embodiments component (c) is a diacid or a monoester of a diacid. For example component (c) may be an optionally substituted phthalic acid or succinic acid derivative. Some especially preferred compounds are hydrocarbyl substituted phthalic acid or succinic acid derivatives wherein the hydrocarbyl substituent has a molecular weight of from 100 to 5000, for example from 200 to 3000.

Other suitable compounds include phthalic acid or succinic acid derivatives having a $C_5$ to $C_{30}$ alkyl or alkenyl substituent.

In some preferred embodiments component (c) is a polyacid or a partial ester of a polyacid. For example component (c) may be an optionally substituted pyromellitic acid derivative. Especially preferred are hydrocarbyl substituted pyromellitic acid derivatives wherein the hydrocarbyl substituent has a molecular weight of from 100 to 5000, preferably from 300 to 4000, suitably from 450 to 2500, for example from 500 to 2000 or from 600 to 1500.

One further polyacid which could be used as component (c) could be a substituted ethylenediaminetetraacetic acid.

Suitably component (c) is an optionally substituted succinic acid derivative and R is $CHR^{10}CHR^{11}COOR^{12}$ wherein each of $R^{10}$, $R^{11}$ and $R^{12}$ is hydrogen or an optionally substituted hydrocarbyl group. Preferably one of $R^{10}$ and $R^{11}$ is hydrogen and the other is an optionally substituted hydrocarbyl group. In some embodiments the optionally substituted hydrocarbyl group is a polyisobutenyl group, preferably having a molecular weight of from 100 to 5000, for example preferably from 200 to 3000. In some embodiments the optionally substituted hydrocarbyl group is a $C_6$ to $C_{30}$ alkyl or alkenyl group, for example a $C_{10}$ to $C_{20}$ alkyl group.

In some embodiments $R^{12}$ is hydrogen. In some embodiments $R^{12}$ is an optionally substituted alkyl group, preferably having 1 to 20 carbon atoms. Suitably $R^{12}$ is an unsubstituted alkyl group, preferably having 1 to 12 carbon atoms. In one embodiment $R^{12}$ is a 2-ethyl hexyl group.

In some embodiments in which $R^{12}$ is not hydrogen, $R^{11}$ has more than 12 carbon atoms, suitably more than 18 carbon atoms.

The present invention may provide a compound of formula:

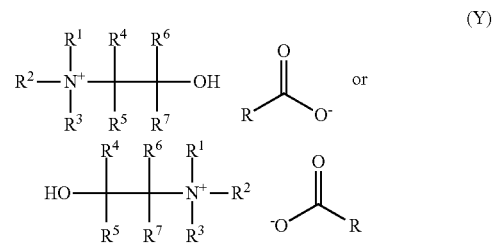

(Y)

wherein $R^1$, $R^2$, $R^3$ $R^4$, $R^5$, $R^6$ and $R^7$ are as defined above and R includes an optionally substituted hydrocarbyl moiety having at least 5 carbon atoms, preferably at least 6 carbon atoms.

The anion RCOO— is suitably the residue of an acid as previously described herein, for example in relation to component (c) above.

The skilled person will appreciate that each of components (a), (b) and (c) used to prepare the quaternary ammonium compounds may be provided as a mixture of compounds, for example a mixture of isomers or oligomers. Thus the resultant quaternary ammonium salts may also comprise a mixture of compounds.

The quaternary ammonium compound of the invention may comprise a mixture of the regioisomers shown in figure Y. It may also comprise a mixture of different optical isomers.

In one embodiment the present invention provides a quaternary ammonium compound which is the reaction product of:

(a) a tertiary amine of formula $R^1R^2R^3N$;

(b) an acid-activated alkylating agent; and (c) an acid including an optionally substituted hydrocarbyl moiety having at least 5 carbon atoms, preferably at least 6 carbon atoms wherein each of $R^1$ and $R^2$ is independently an optionally substituted alkyl or alkenyl group and $R^3$ is selected from:

(x) an optionally substituted alkylene phenol moiety of formula (A) or (B)

(A)

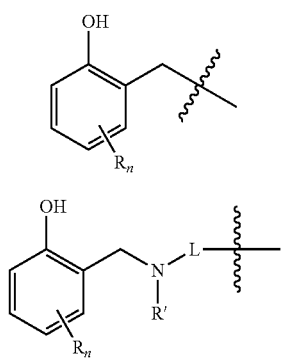

(B)

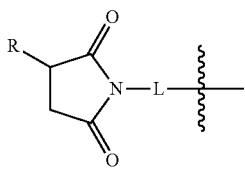

wherein n is 0 to 4, preferably 1, R is an optionally substituted hydrocarbyl group, R' is an optionally substituted alkyl, alkenyl or aryl group; and L is a linking group;

(y) a succinimide moiety of formula:

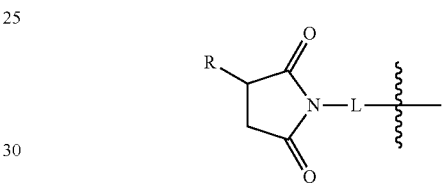

wherein R is an optionally substituted hydrocarbyl group and L is a linking group; and (z) a polyisobutenyl group having a molecular weight of from 100 to 500, preferably from 500 to 2000.

Suitably in one embodiment of the present invention component (a) is selected from a tertiary amine including a polyisobutylene substituent; a Mannich reaction product including a tertiary amine; and a substituted acylated amine or alcohol including a tertiary amine; and component (c) is selected from a monoacid, a diacid or a monoester of a diacid.

Suitably in one embodiment of the present invention component (a) is selected from a tertiary amine including a polyisobutylene substituent; a Mannich reaction product including a tertiary amine; and a substituted acylated amine or alcohol including a tertiary amine; and component (c) is selected from a diacid or a monoester of a diacid.

Suitably in one embodiment of the present invention component (a) is selected from a tertiary amine including a polyisobutylene substituent, a Mannich reaction product including a tertiary amine and a substituted acylated amine or alcohol including a tertiary amine; and component (c) is a monoester of a diacid.

In one embodiment the present invention provides a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms;

wherein each of $R^1$ and $R^2$ is independently an optionally substituted alkyl or alkenyl group and $R^3$ is a succinimide moiety of formula:

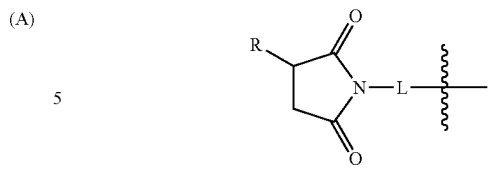

wherein R is an optionally substituted hydrocarbyl group and L is a linking group; and component (c) is selected from a monoacid, a diacid or a monoester of a diacid.

In one embodiment the present invention provides a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms;

wherein each of $R^1$ and $R^2$ is independently an optionally substituted alkyl or alkenyl group and $R^3$ is a succinimide moiety of formula:

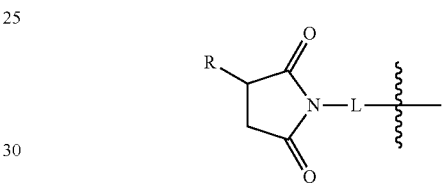

wherein R is an optionally substituted hydrocarbyl group and L is a linking group; and component (c) is selected from a diacid and a monoester of a diacid.

In one embodiment the present invention provides a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms.

wherein each of $R^1$ and $R^2$ is independently an optionally substituted alkyl or alkenyl group and $R^3$ is a succinimide moiety of formula:

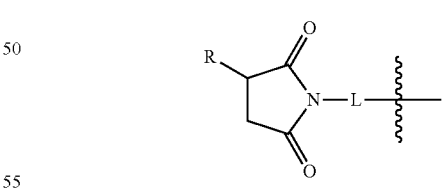

wherein R is an optionally substituted hydrocarbyl group and L is a linking group; and component (c) is a monoester of a diacid.

In one embodiment the present invention provided a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms;

wherein each of $R^1$ and $R^2$ is independently an optionally substituted alkyl or alkenyl group and $R^3$ is a succinimide moiety of formula:

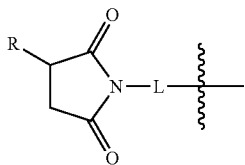

wherein R is an optionally substituted hydrocarbyl group and L is a linking group; and component (c) is a monoacid.

In one embodiment the present invention provides a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms;
wherein each of $R^1$ and $R^2$ is independently an optionally substituted alkyl or alkenyl group and $R^3$ is a succinimide moiety of formula:

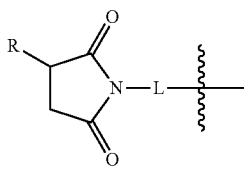

wherein R is an optionally substituted hydrocarbyl group and L is a linking group; and component (c) an optionally substituted succinic acid derivative of formula $HOOC(CH)R^{10}CHR^{11}COOR^{12}$ wherein each of $R^{10}$, $R^{11}$ and $R^{12}$ is hydrogen or an optionally substituted hydrocarbyl group. Preferably one of $R^{10}$ and $R^{11}$ is hydrogen and the other is an optionally substituted hydrocarbyl group. The optionally substituted hydrocarbyl group is preferably a polyisobutenyl group, preferably having a molecular weight of from 100 to 5000, preferably from 300 to 4000, suitably from 450 to 2500, for example from 500 to 2000 or from 600 to 1500. In one preferred embodiment R12 is an optionally substituted hydrocarbyl group, preferably a $C_1$ to $C_{30}$ alkyl group.

In one embodiment the present invention provides a quaternary ammonium compound which is the reaction product of:
(a) a tertiary amine of formula $R^1R^2R^3N$;
(b) an acid-activated alkylating agent; and
(c) an acid including an optionally substituted hydrocarbyl moiety having at least 5 carbon atoms, preferably at least 6 carbon atoms;
wherein each of $R^1$ and $R^2$ is independently an optionally substituted alkyl or alkenyl group and $R^3$ is an optionally substituted alkyl or alkenyl group having from 1 to 30 carbon atoms and component (c) is a diacid.

In some embodiments component (a) comprises a tertiary amine of formula $R^1R^2R^3N$ wherein each of $R^1$, $R^2$ and $R^3$ is independently selected from an alkyl or hydroxyalkyl group having 1 to 10 carbon atoms; and component (c) is a diacid.

In some embodiments in which component (c) is monoester of a diacid or a partial ester of a polyacid component (a) is not a tertiary amine of formula $R^1R^2R^3N$ wherein each of $R^1$, $R^2$ and $R^3$ is independently selected from an alkyl or hydroxyalkyl group having 1 to 10 carbon atoms.

The second aspect of the present invention provides a method of preparing a quaternary ammonium salt. Suitable conditions for carrying out such reactions are known to the person skilled in the art and may be as described in relation to the examples.

The quaternary ammonium compounds of the present invention have been found to be effective as detergent additives for use in fuel or lubricating additives.

Thus the present invention provides the use of a quaternary ammonium compound of the first aspect as an additive for fuel or lubricating oil compositions.

The present invention may provide the use of a quaternary ammonium compound of the first aspect as a detergent additive for fuel or lubricating oil compositions.

The present invention may provide the use of a quaternary ammonium compound of the first aspect as a detergent additive for lubricating oil compositions.

The present invention may provide the use of a quaternary ammonium compound of the first aspect as a detergent additive for fuel compositions.

The present invention may provide the use of a quaternary ammonium compound of the first aspect as a detergent additive for gasoline or diesel fuel compositions.

The present invention may provide the use of a quaternary ammonium compound of the first aspect as a detergent additive for gasoline fuel compositions.

The present invention may provide the use of a quaternary ammonium compound of the first aspect as a detergent additive for diesel fuel compositions.

According to a third aspect of the present invention there is provided an additive composition comprising a quaternary ammonium salt of the first aspect and a diluent or carrier.

The additive composition of the third aspect may be an additive composition for lubricating oil.

The additive composition of the third aspect may be an additive composition for gasoline.

Preferably the additive composition of the third aspect is an additive composition for diesel fuel.

The quaternary ammonium compound is suitably present in the additive composition in an amount of from 1 to 99 wt %, for example from 1 to 75 wt %.

The additive composition may comprise a mixture of two or more quaternary ammonium compounds of the present invention. In such embodiments the above amounts suitably refer to the total amount of all such compounds present in the composition.

The additive composition may include one or more further additives. These may be selected from antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers, friction modifiers, and conductivity improvers.

In some preferred embodiments the additive composition includes one or more further nitrogen-containing detergents.

The present invention may provide a fuel or lubricating oil composition comprising a quaternary ammonium salt of the first aspect.

According to a fourth aspect of the present invention there is provided a lubricating composition comprising an oil of lubricating viscosity and as an additive a quaternary ammonium compound of formula (X):

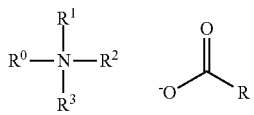

(X)

wherein $R^0$, $R^1$, $R^2$ and $R^3$ is each individually an optionally substituted alkyl, alkenyl and aryl group and R includes an optionally substituted hydrocarbyl moiety having at least 5 carbon atoms.

In preferred embodiments the fourth aspect of the present invention provides a lubricating composition comprising an oil of lubricating viscosity and as an additive a quaternary ammonium compound which is the reaction product of:
(a) a tertiary amine;
(b) an acid-activated alkylating agent; and
(c) an acid including an optionally substituted alkyl or alkenyl moiety having at least 5 carbon atoms, preferably at least 6 carbon atoms.

Preferred features of the quaternary ammonium compound are as defined in relation to the first aspect.

The additive composition of the third aspect suitably upon dilution with an oil of lubricating viscosity provides a lubricating composition of the fourth aspect.

According to a fifth aspect of the present invention there is provided a fuel composition comprising as an additive a quaternary ammonium compound of formula (X):

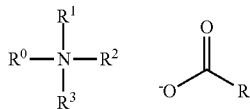

(X)

wherein $R^0$, $R^1$, $R^2$ and $R^3$ is each individually an optionally substituted alkyl, alkenyl and aryl group and R includes an optionally substituted hydrocarbyl moiety having at least 5 carbon atoms.

In preferred embodiments the fifth aspect of the present invention provides a fuel composition comprising as an additive a quaternary ammonium compound which is the reaction product of:
(a) a tertiary amine;
(b) an acid-activated alkylating agent; and
(c) an acid including an optionally substituted alkyl or alkenyl moiety having at least 5 carbon atoms, preferably at least 6 carbon atoms.

Preferred features of the quaternary ammonium compound are as defined in relation to the first aspect.

The additive composition of the third aspect suitably upon dilution with fuel provides a fuel composition of the fifth aspect.

The present invention may further provide a method of preparing a fuel composition, the method comprising preparing a quaternary ammonium salt according to the method of the second aspect, and mixing the quaternary ammonium salt into the fuel.

Preferably the present invention provides a fuel composition comprising as an additive a quaternary ammonium compound which is the reaction product of:
(a) a tertiary amine;
(b) an epoxide; and
(c) an acid including an optionally substituted alkyl or alkenyl moiety having at least 5 carbon atoms, preferably at least 6 carbon atoms.

The fuel composition of the fifth aspect of the present invention may be a gasoline composition or a diesel fuel composition. Preferably it is a diesel fuel composition.

By diesel fuel we include any fuel suitable for use in a diesel engine either for road use or non-road use. This includes but is not limited to fuels described as diesel, marine diesel, heavy fuel oil, industrial fuel oil, etc.

The diesel fuel composition of the present invention may comprise a petroleum-based fuel oil, especially a middle distillate fuel oil. Such distillate fuel oils generally boil within the range of from 110° C. to 500° C., e.g. 150° C. to 400° C. The diesel fuel may comprise atmospheric distillate or vacuum distillate, cracked gas oil, or a blend in any proportion of straight run and refinery streams such as thermally and/or catalytically cracked and hydro-cracked distillates.

The diesel fuel composition of the present invention may comprise non-renewable Fischer-Tropsch fuels such as those described as GTL (gas-to-liquid) fuels, CTL (coal-to-liquid) fuels and OTL (oil sands-to-liquid).

The diesel fuel composition of the present invention may comprise a renewable fuel such as a biofuel composition or biodiesel composition.

The diesel fuel composition may comprise first generation biodiesel. First generation biodiesel contains esters of, for example, vegetable oils, animal fats and used cooking fats. This form of biodiesel may be obtained by transesterification of oils, for example rapeseed oil, soybean oil, safflower oil, palm 25 oil, corn oil, peanut oil, cotton seed oil, tallow, coconut oil, physic nut oil (Jatropha), sunflower seed oil, used cooking oils, hydrogenated vegetable oils or any mixture thereof, with an alcohol, usually a monoalcohol, usually in the presence of a catalyst.

The diesel fuel composition may comprise second generation biodiesel. Second generation biodiesel is derived from renewable resources such as vegetable oils and animal fats and processed, often in the refinery, often using hydroprocessing such as the H-Bio process developed by Petrobras. Second generation biodiesel may be similar in properties and quality to petroleum based fuel oil streams, for example renewable diesel produced from vegetable oils, animal fats etc. and marketed by ConocoPhillips as Renewable Diesel and by Neste as NExBTL.

The diesel fuel composition of the present invention may comprise third generation biodiesel. Third generation biodiesel utilises gasification and Fischer-Tropsch technology including those described as BTL (biomass-to-liquid) fuels. Third generation biodiesel does not differ widely from some second generation biodiesel, but aims to exploit the whole plant (biomass) and thereby widens the feedstock base.

The diesel fuel composition may contain blends of any or all of the above diesel fuel compositions.

In some embodiments the diesel fuel composition of the present invention may be a blended diesel fuel comprising bio-diesel. In such blends the bio-diesel may be present in an amount of, for example up to 0.5%, up to 1%, up to 2%, up to 3%, up to 4%, up to 5%, up to 10%, up to 20%, up to 30%, up to 40%, up to 50%, up to 60%, up to 70%, up to 80%, up to 90%, up to 95% or up to 99%.

In some embodiments the fuel composition may comprise neat biodiesel.

In some embodiments the fuel composition may comprise a neat GTL fuel.

In some embodiments the diesel fuel composition may comprise a secondary fuel, for example ethanol. Preferably however the diesel fuel composition does not contain ethanol.

The diesel fuel composition of the present invention may contain a relatively high sulphur content, for example greater than 0.05% by weight, such as 0.1% or 0.2%.

However in preferred embodiments the diesel fuel has a sulphur content of at most 0.05% by weight, more preferably of at most 0.035% by weight, especially of at most 0.015%. Fuels with even lower levels of sulphur are also suitable such as, fuels with less than 50 ppm sulphur by weight, preferably less than 20 ppm, for example 10 ppm or less.

Suitably the quaternary ammonium salt additive is present in the diesel fuel composition in an amount of at least 0.1 ppm, preferably at least 1 ppm, more preferably at least 5 ppm, suitably at least 10 ppm, for example at least 20 ppm or at least 25 ppm.

Suitably the quaternary ammonium salt additive is present in the diesel fuel composition in an amount of less than 10000 ppm, preferably less than 1000 ppm, preferably less than 500 ppm, preferably less than 250 ppm, suitably less than 200 ppm, for example less than 150 ppm, or less than 100 ppm.

The diesel fuel composition of the fifth aspect of the present invention may comprise a mixture of two or more quaternary ammonium salts of the first aspect. In such embodiments the above amounts refer to the total amounts of all such additives present in the composition.

The diesel fuel composition of the present invention may include one or more further additives such as those which are commonly found in diesel fuels. These include, for example, antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers. Examples of suitable amounts of each of these types of additives will be known to the person skilled in the art.

In some preferred embodiments the diesel fuel composition of the present invention comprises one or more further detergents. Nitrogen-containing detergents are preferred.

The one or more further detergents may be selected from:
(i) an additional quaternary ammonium salt additive which is not a quaternary ammonium compound of the first aspect;
(ii) the product of a Mannich reaction between an aldehyde, an amine and an optionally substituted phenol;
(iii) the reaction product of a carboxylic acid-derived acylating agent and an amine;
(iv) the reaction product of a carboxylic acid-derived acylating agent and hydrazine;
(v) a salt formed by the reaction of a carboxylic acid with di-n-butylamine or tri-n-butylamine;
(vi) the reaction product of an optionally substituted hydrocarbyl-substituted dicarboxylic acid or anhydride and an amine compound or salt which product comprises at least one amino triazole group; and
(vii) a substituted polyaromatic detergent additive.

In some embodiments the diesel fuel composition comprises an additional quaternary ammonium salt additive which is not a quaternary ammonium compound of the first aspect.

The additional quaternary ammonium salt additive is suitably the reaction product of a nitrogen-containing species having at least one tertiary amine group and a quaternising agent.

The nitrogen containing species may be selected from:
(x) the reaction product of an optionally substituted hydrocarbyl-substituted acylating agent and a compound comprising at least one tertiary amine group and a primary amine, secondary amine or alcohol group;
(y) a Mannich reaction product comprising a tertiary amine group; and
(z) a polyalkylene substituted amine having at least one tertiary amine group.

Examples of quaternary ammonium salt and methods for preparing the same are described in the following patents, which are hereby incorporated by reference, US2008/0307698, US2008/0052985, US2008/0113890 and US2013/031827.

Component (x) may be regarded as the reaction product of an optionally substituted hydrocarbyl-substituted acylating agent and a compound having an oxygen or nitrogen atom capable of condensing with said acylating agent and further having a tertiary amino group. Preferred features of these compounds are as described above in relation to tertiary amine component (a) used to prepare the quaternary ammonium salt additives of the present invention.

The preparation of some suitable quaternary ammonium salt additives in which the nitrogen-containing species includes component (x) is described in WO 2006/135881 and WO2011/095819.

Component (y) is a Mannich reaction product having a tertiary amine. The preparation of quaternary ammonium salts formed from nitrogen-containing species including component (y) is described in US 2008/0052985. Preferred features of these compounds are as described above in relation to tertiary amine component (a) used to prepare the quaternary ammonium salt additives of the present invention.

The preparation of quaternary ammonium salt additives in which the nitrogen-containing species includes component (z) is described for example in US 2008/0113890. Preferred features of these compounds are as described above in relation to tertiary amine component (a) used to prepare the quaternary ammonium salt additives of the present invention.

To form the additional quaternary ammonium salt additives (I), the nitrogen containing species having a tertiary amine group is reacted with a quaternizing agent.

The quaternising agent may suitably be selected from esters and non-esters.

In some preferred embodiments, quaternising agents used to form the quaternary ammonium salt additives of the present invention are esters.

Preferred ester quaternising agents are compounds of formula (III):

in which R is an optionally substituted alkyl, alkenyl, aryl or alkylaryl group and $R^1$ is a $C_1$ to $C_{22}$ alkyl, aryl or alkylaryl group. The compound of formula (III) is suitably an ester of a carboxylic acid capable of reacting with a tertiary amine to form a quaternary ammonium salt.

Suitable quaternising agents include esters of carboxylic acids having a pKa of 3.5 or less.

The compound of formula (III) is preferably an ester of a carboxylic acid selected from a substituted aromatic carboxylic acid, an α-hydroxycarboxylic acid and a polycarboxylic acid.

In some preferred embodiments the compound of formula (III) is an ester of a substituted aromatic carboxylic acid and thus R is a substituted aryl group.

Especially preferred compounds of formula (III) are lower alkyl esters of salicylic acid such as methyl salicylate, ethyl salicylate, n and i-propyl salicylate, and butyl salicylate, preferably methyl salicylate.

In some embodiments the compound of formula (III) is an ester of an α-hydroxycarboxylic acid. In such embodiments the compound has the structure:

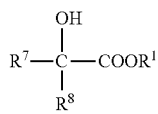

wherein $R^7$ and $R^8$ are the same or different and each is selected from hydrogen, alkyl, alkenyl, aralkyl or aryl. Compounds of this type suitable for use herein are described in EP 1254889.

A preferred compound of this type is methyl 2-hydroxyisobutyrate.

In some embodiments the compound of formula (III) is an ester of a polycarboxylic acid. In this definition we mean to include dicarboxylic acids and carboxylic acids having more than 2 acidic moieties.

One especially preferred compound of formula (III) is dimethyl oxalate.

The ester quaternising agent may be selected from an ester of a carboxylic acid selected from one or more of oxalic acid, tartaric acid, phthalic acid, salicylic acid, maleic acid, malonic acid, citric acid, nitrobenzoic acid, aminobenzoic acid and 2, 4, 6-trihydroxybenzoic acid.

Preferred ester quaternising agents include dimethyl oxalate, methyl 2-nitrobenzoate, dimethyl phthalate, dimethyl tartrate and methyl salicylate.

Suitable non-ester quaternising agents include dialkyl sulfates, benzyl halides, hydrocarbyl substituted carbonates, hydrocarbyl substituted epoxides in combination with an acid, alkyl halides, alkyl sulfonates, sultones, hydrocarbyl substituted phosphates, hydrocarbyl substituted borates, alkyl nitrites, alkyl nitrates, hydroxides, N-oxides or mixtures thereof.

In some embodiments the quaternary ammonium salt may be prepared from, for example, an alkyl or benzyl halide (especially a chloride) and then subjected to an ion exchange reaction to provide a different anion as part of the quaternary ammonium salt. Such a method may be suitable to prepare quaternary ammonium hydroxides, alkoxides, nitrites or nitrates.

Preferred non-ester quaternising agents include dialkyl sulfates, benzyl halides, hydrocarbyl substituted carbonates, hydrocarbyl substituted epoxides in combination with an acid, alkyl halides, alkyl sulfonates, sultones, hydrocarbyl substituted phosphates, hydrocarbyl substituted borates, N-oxides or mixtures thereof.

Suitable dialkyl sulfates for use herein as quaternising agents include those including alkyl groups having 1 to 10 carbons atoms in the alkyl chain. A preferred compound is dimethyl sulfate.

Suitable benzyl halides include chlorides, bromides and iodides. A preferred compound is benzyl bromide.

Suitable hydrocarbyl substituted carbonates may include two hydrocarbyl groups, which may be the same or different. Preferred compounds of this type include diethyl carbonate and dimethyl carbonate.

Suitable hydrocarbyl substituted epoxides have the formula:

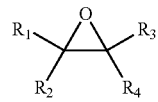

wherein each of $R^1$, $R^2$, $R^3$ and $R^4$ is independently hydrogen or an optionally substituted hydrocarbyl group having 1 to 50 carbon atoms. Examples of suitable epoxides include ethylene oxide, propylene oxide, butylene oxide, styrene oxide and stillbene oxide. The hydrocarbyl epoxides are used as quaternising agents in combination with an acid. In such embodiments the acid is not an acid of the type defined in relation to component (c) used to prepare the quaternary ammonium salts of the present invention.

In embodiments in which the hydrocarbyl substituted acylating agent has more than one acyl group, and is reacted with the compound of formula (I) or formula (II) is a dicarboxylic acylating agent no separate acid needs to be added. However in other embodiments an acid such as acetic acid may be used.

Especially preferred epoxide quaternising agents are propylene oxide and styrene oxide.

Suitable sultones include propane sultone and butane sultone.

Suitable hydrocarbyl substituted phosphates include dialkyl phosphates, trialkyl phosphates and O,O-dialkyl dithiophosphates.

Suitable hydrocarbyl substituted borate groups include alkyl borates having 1 to 12 carbon atoms.

Preferred alkyl nitrites and alkyl nitrates have 1 to 12 carbon atoms.

Preferably the non-ester quaternising agent is selected from dialkyl sulfates, benzyl halides, hydrocarbyl substituted carbonates, hydrocarbyl substituted epoxides in combination with an acid, and mixtures thereof.

Especially preferred non-ester quaternising agents for use herein are hydrocarbyl substituted epoxides in combination with an acid. These may include embodiments in which a separate acid is provided or embodiments in which the acid is provided by the tertiary amine compound that is being quaternised. Preferably the acid is provided by the tertiary amine molecule that is being quaternised.

Preferred quaternising agents for use herein include dimethyl oxalate, methyl 2-nitrobenzoate, methyl salicylate and styrene oxide or propylene oxide optionally in combination with an additional acid.

For the avoidance of doubt, in such embodiments the additional acid is not an acid including an optionally substituted hydrocarbyl moiety having at least 5 carbon atoms as defined in the first aspect.

An especially preferred additional quaternary ammonium salt for use herein is formed by reacting methyl salicylate or dimethyl oxalate with the reaction product of a polyisobutylene-substituted succinic anhydride having a PIB molecular weight of 700 to 1300 and dimethylaminopropylamine.

Other suitable additional quaternary ammonium salts include quaternised terpolymers, for example as described in US2011/0258917; quaternised copolymers, for example as described in US2011/0315107; and the acid-free quaternised nitrogen compounds disclosed in US2012/0010112.

Further suitable additional quaternary ammonium compounds for use in the present invention include the quaternary ammonium compounds described in the applicants copending application WO2013/017889.

In some embodiments the diesel fuel composition comprises the product of a Mannich reaction between an aldehyde, an amine and an optionally substituted phenol. This Mannich reaction product is suitably not a quaternary ammonium salt.

Preferably the aldehyde component used to prepare the Mannich additive is an aliphatic aldehyde. Preferably the aldehyde has 1 to 10 carbon atoms. Most preferably the aldehyde is formaldehyde.

The amine used to prepare the Mannich additive is preferably a polyamine. This may be selected from any compound including two or more amine groups. Preferably the polyamine is a polyalkylene polyamine, preferably a polyethylene polyamine. Most preferably the polyamine comprises tetraethylenepentamine or ethylenediamine.

The optionally substituted phenol component used to prepare the Mannich additive may be substituted with 0 to 4 groups on the aromatic ring (in addition to the phenol OH). For example it may be a hydrocarbyl-substituted cresol. Most preferably the phenol component is a mono-substituted phenol. Preferably it is a hydrocarbyl substituted phenol. Preferred hydrocarbyl substituents are alkyl substituents having 4 to 28 carbon atoms, especially 10 to 14 carbon atoms. Other preferred hydrocarbyl substituents are polyalkenyl substituents such polyisobutenyl substituents having an average molecular weight of from 400 to 2500, for example from 500 to 1500.

In some embodiments the diesel fuel composition comprises the reaction product of a carboxylic acid-derived acylating agent and an amine.

These may also be referred to herein in general as acylated nitrogen-containing compounds.

Suitable acylated nitrogen-containing compounds may be made by reacting a carboxylic acid acylating agent with an amine and are known to those skilled in the art.

Preferred acylated nitrogen-containing compounds are substituted with an optionally substituted hydrocarbyl group. The hydrocarbyl substituent may be in either the carboxylic acid acylating agent derived portion of the molecule or in the amine derived portion of the molecule, or both. Preferably, however, it is in the acylating agent portion. A preferred class of acylated nitrogen-containing compounds suitable for use in the present invention are those formed by the reaction of an acylating agent having a hydrocarbyl substituent of at least 8 carbon atoms and a compound comprising at least one primary or secondary amine group.

The acylating agent may be a mono- or polycarboxylic acid (or reactive equivalent thereof) for example a substituted succinic, phthalic or propionic acid or anhydride.

The term "hydrocarbyl" is previously defined herein. The hydrocarbyl substituent in such acylating agents preferably comprises at least 10, more preferably at least 12, for example at least 30 or at least 40 carbon atoms. It may comprise up to about 200 carbon atoms. Preferably the hydrocarbyl substituent of the acylating agent has a number average molecular weight (Mn) of between 170 to 2800, for example from 250 to 1500, preferably from 500 to 1500 and more preferably 500 to 1100. An Mn of 700 to 1300 is especially preferred. In a particularly preferred embodiment, the hydrocarbyl substituent has a number average molecular weight of 700-1000, preferably 700-850 for example 750.

Preferred hydrocarbyl-based substituents are polyisobutenes. Such compounds are known to the person skilled in the art.

Preferred hydrocarbyl substituted acylating agents are polyisobutenyl succinic anhydrides. These compounds are commonly referred to as "PIBSAs" and are known to the person skilled in the art.

Conventional polyisobutenes and so-called "highly-reactive" polyisobutenes are suitable for use in the invention.

Especially preferred PIBSAs are those having a PIB molecular weight (Mn) of from 300 to 2800, preferably from 450 to 2300, more preferably from 500 to 1300.

To prepare these additives the carboxylic acid-derived acylating agent is reacted with an amine. Suitably it is reacted with a primary or secondary amine. Examples of suitable amines are known to the person skilled in the art and include polyalkylene polyamines, heterocyclic-substituted polyamines and aromatic polyamines.

Preferred amines are polyethylene polyamines including ethylenediamine, diethylenetriamine, triethylenetetramine, tetraethylenepentamine, pentaethylenehexamine, hexaethylene-heptamine, and mixtures and isomers thereof.

In preferred embodiments the reaction product of the carboxylic acid derived acylating agent and an amine includes at least one primary or secondary amine group.

A preferred acylated nitrogen-containing compound for use herein is prepared by reacting a poly(isobutene)-substituted succinic acid-derived acylating agent (e.g., anhydride, acid, ester, etc.) wherein the poly(isobutene) substituent has a number average molecular weight (Mn) of between 170 to 2800 with a mixture of ethylene polyamines having 2 to about 9 amino nitrogen atoms, preferably about 2 to about 8 nitrogen atoms, per ethylene polyamine and about 1 to about 8 ethylene groups. These acylated nitrogen compounds are suitably formed by the reaction of a molar ratio of acylating agent:amino compound of from 10:1 to 1:10, preferably from 5:1 to 1:5, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. Acylated amino compounds of this type and their preparation are well known to those skilled in the art and are described in for example EP0565285 and U.S. Pat. No. 5,925,151.

In some preferred embodiments the composition comprises a detergent of the type formed by the reaction of a polyisobutene-substituted succinic acid-derived acylating agent and a polyethylene polyamine. Suitable compounds are, for example, described in WO2009/040583.

In some embodiments the diesel fuel composition comprises the reaction product of a carboxylic acid-derived acylating agent and hydrazine.

Suitably the additive comprises the reaction product between a hydrocarbyl-substituted succinic acid or anhydride and hydrazine.

Preferably, the hydrocarbyl group of the hydrocarbyl-substituted succinic acid or anhydride comprises a $C_8$-$C_{36}$ group, preferably a $C_8$-$C_{18}$ group. Alternatively, the hydrocarbyl group may be a polyisobutylene group with a number average molecular weight of between 200 and 2500, preferably between 800 and 1200.

Hydrazine has the formula $NH_2—NH_2$ Hydrazine may be hydrated or non-hydrated. Hydrazine monohydrate is preferred.

The reaction between the hydrocarbyl-substituted succinic acid or anhydride and hydrazine produces a variety of products, such as is disclosed in US 2008/0060259.

In some embodiments the diesel fuel composition comprises a salt formed by the reaction of a carboxylic acid with di-n-butylamine or tri-n-butylamine. Exemplary compounds of this type are described in US 2008/0060608.

Such additives may suitably be the di-n-butylamine or tri-n-butylamine salt of a fatty acid of the formula $[R'(COOH)_x]_y$, where each R' is independently a hydrocarbon group of between 2 and 45 carbon atoms, and x is an integer between 1 and 4.

In a preferred embodiment, the carboxylic acid comprises tall oil fatty acid (TOFA).

Further preferred features of additives of this type are described in US2008/0060608.

In some embodiments the diesel fuel composition comprises the reaction product of a hydrocarbyl-substituted dicarboxylic acid or anhydride and an amine compound or salt which product comprises at least one amino triazole group.

Additives of this type are suitably the reaction product of a hydrocarbyl substituted dicarboxylic acid or anhydride and an amine compound having the formula:

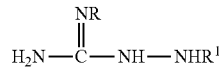

wherein R is selected from the group consisting of a hydrogen and a hydrocarbyl group containing from about 1 to about 15 carbon atoms, and $R^1$ is selected from the group consisting of hydrogen and a hydrocarbyl group containing from about 1 to about 20 carbon atoms.

The additive suitably comprises the reaction product of an amine compound having the formula:

and a hydrocarbyl carbonyl compound of the formula:

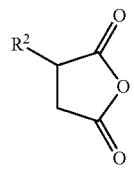

wherein $R^2$ is a hydrocarbyl group having a number average molecular weight ranging from about 100 to about 5000, preferably from 200 to 3000.

Without being bound by theory, it is believed that the reaction product of the amine and hydrocarbyl carbonyl compound is an aminotriazole, such as a bis-aminotriazole compound of the formula:

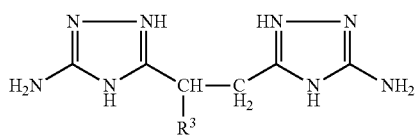

including tautomers having a number average molecular weight ranging from about 200 to about 3000 containing from about 40 to about 80 carbon atoms. The five-membered ring of the triazole is considered to be aromatic.

Further preferred features of additive compounds of this type are as defined in US2009/0282731.

In some embodiments the diesel fuel composition comprises a substituted polyaromatic detergent additive.

One preferred compound of this type is the reaction product of an ethoxylated naphthol and paraformaldehyde which is then reacted with a hydrocarbyl substituted acylating agent.

Further preferred features of these detergents are described in EP1884556.

In some embodiments the fuel composition may be a gasoline fuel composition.

Suitably the quaternary ammonium salt additive is present in the gasoline fuel composition in an amount of at least 0.1 ppm, preferably at least 1 ppm, more preferably at least 5 ppm, suitably at least 10 ppm, for example at least 20 ppm or at least 25 ppm.

Suitably the quaternary ammonium salt additive is present in the gasoline fuel composition in an amount of less than 10000 ppm, preferably less than 1000 ppm, preferably less than 500 ppm, preferably less than 250 ppm, suitably less than 200 ppm, for example less than 150 ppm, or less than 100 ppm.

The gasoline fuel composition of the fifth aspect of the present invention may comprise a mixture of two or more quaternary ammonium salts of the first aspect. In such embodiments the above amounts refer to the total amounts of all such additives present in the composition.

In such embodiments the composition may comprise one or more gasoline detergents selected from:
(p) hydrocarbyl—substituted polyoxyalkylene amines or polyetheramines;
(q) acylated nitrogen compounds which are the reaction product of a carboxylic acid-derived acylating agent and an amine;
(r) hydrocarbyl-substituted amines wherein the hydrocarbyl substituent is substantially aliphatic and contains at least 8 carbon atoms;
(s) Mannich base additives comprising nitrogen-containing condensates of a phenol, aldehyde and primary or secondary amine;
(t) aromatic esters of a polyalkylphenoxyalkanol;
(u) an additional quaternary ammonium salt additive which is not a quaternary ammonium compound of the first aspect; and
(v) tertiary hydrocarbyl amines having a maximum of 30 carbon atoms.

Suitable hydrocarbyl-substituted polyoxyalkylene amines or polyetheramines (p) are described in U.S. Pat. No. 6,217,624 and U.S. Pat. No. 4,288,612. Other suitable polyetheramines are those taught in U.S. Pat. No. 5,089,029 and U.S. Pat. No. 5,112,364.

The gasoline composition of the present invention may comprise as an additive acylated nitrogen compounds (q) which are the reaction product of a carboxylic acid-derived acylating agent and an amine. Such compounds are preferably as previously defined herein in relation to component (iii) of the additives which may be added to the diesel fuel compositions of the invention.

Hydrocarbyl-substituted amines (r) suitable for use in the gasoline fuel compositions of the present invention are well known to those skilled in the art and are described in a number of patents. Among these are U.S. Pat. Nos. 3,275,554; 3,438,757; 3,454,555; 3,565,804; 3,755,433 and 3,822,209. These patents describe suitable hydrocarbyl amines for use in the present invention including their method of preparation.

The Mannich additives (s) comprise nitrogen-containing condensates of a phenol, aldehyde and primary or secondary amine, and are suitably as defined in relation to component (ii) of the additives suitable for use in diesel fuel compositions.

The gasoline compositions of the present invention may further comprise as additives (t) aromatic esters of a polyalkylphenoxyalkanol.

The aromatic ester component which may be employed additive composition is an aromatic ester of a polyalkylphenoxyalkanol and has the following general formula:

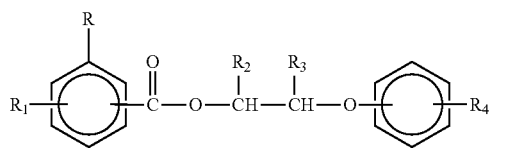

(I)

or a fuel-soluble salt(s) thereof wherein R is hydroxy, nitro or —(CH2)x-NR$_5$R$_6$, wherein R$_5$ and R$_6$ are independently hydrogen or lower alkyl having 1 to 6 carbon atoms and x is 0 or 1;

R$_1$ is hydrogen, hydroxy, nitro or —NR$_7$R$_5$ wherein R$_7$ and R$_5$ are independently hydrogen or lower alkyl having 1 to 6 carbon atoms;

R$_2$ and R$_3$ are independently hydrogen or lower alkyl having 1 to 6 carbon atoms; and R$_4$ is a polyalkyl group having an average molecular weight in the range of about 450 to 5,000.

Preferred features of these aromatic ester compounds are as described in WO2011141731.

The additional quaternary ammonium salt additives (u) are suitably as defined in relation to component (i) of the additives suitable for use in diesel fuel compositions.

Tertiary hydrocarbyl amines (v) suitable for use in the gasoline fuel compositions of the present invention are tertiary amines of the formula R$^1$R$^2$R$^3$N wherein R$^1$, R$^2$ and R$^3$ are the same or different C$_1$-C$_{20}$ hydrocarbyl residues and the total number of carbon atoms is no more than 30. Suitable examples are N,N dimethyl n dodecylamine, 3-(N, N-dimethylamino) propanol and N,N-di(2-hydroxyethyl)-oleylamine. Preferred features of these tertiary hydrocarbyl amines are as described in US2014/0123547.

The gasoline composition may further comprise a carrier oil.

The carrier oil may have any suitable molecular weight. A preferred molecular weight is in the range 500 to 5000.

In one embodiment the carrier oil may comprise an oil of lubricating viscosity, including natural or synthetic oils of lubricating viscosity, oil derived from hydrocracking, hydrogenation, hydrofinishing, unrefined, refined and re-refined oils, or mixtures thereof.

Natural oils include animal oils, vegetable oils, mineral oils or mixtures thereof. Synthetic oils may include hydrocarbon oils such as those produced by Fischer-Tropsch reactions and typically may be hydroisomerised Fischer-Tropsch hydrocarbons or waxes.

In another embodiment the carrier oil may comprise a polyether carrier oil. In a preferred embodiment the polyether carrier oil is a mono end-capped polyalkylene glycol, especially a mono end-capped polypropylene glycol. Carrier oils of this type will be known to the person skilled in the art.

The gasoline fuel compositions of the invention may contain one or more further additives conventionally added to gasoline, for example other detergents, dispersants, antioxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers and combustion improvers.

The quaternary ammonium salts of the present invention are useful as detergent additives for fuel and lubricating oil compositions. The inclusion of these additives in fuel compositions has been found to reduce deposits within engines in which the fuel is combusted. This may be achieved by preventing or reducing the formation of deposits, i.e. keeping the engine clean, or may aid the removal of existing deposits, i.e. cleaning up a fouled engine.

The quaternary ammonium compounds of the present invention have been found to be particularly effective in diesel engines, especially in modern diesel engines having a high pressure fuel system.

Due to consumer demand and legislation, diesel engines have in recent years become much more energy efficient, show improved performance and have reduced emissions.

These improvements in performance and emissions have been brought about by improvements in the combustion process. To achieve the fuel atomisation necessary for this improved combustion, fuel injection equipment has been developed which uses higher injection pressures and reduced fuel injector nozzle hole diameters. The fuel pressure at the injection nozzle is now commonly in excess of 1500 bar (1.5×10$^8$ Pa). To achieve these pressures the work that must be done on the fuel also increases the temperature of the fuel. These high pressures and temperatures can cause degradation of the fuel. Furthermore, the timing, quantity and control of fuel injection has become increasingly precise. This precise fuel metering must be maintained to achieve optimal performance.

Diesel engines having high pressure fuel systems can include but are not limited to heavy duty diesel engines and smaller passenger car type diesel engines. Heavy duty diesel engines can include very powerful engines such as the MTU series 4000 diesel having 20 cylinder variants designed primarily for ships and power generation with power output up to 4300 kW or engines such as the Renault dXi 7 having 6 cylinders and a power output around 240 kW. A typical passenger car diesel engine is the Peugeot DW10 having 4 cylinders and power output of 100 kW or less depending on the variant.

In preferred diesel engines relating to this invention, a common feature is a high pressure fuel system. Typically pressures in excess of 1350 bar (1.35×10$^8$ Pa) are used but often pressures of up to 2000 bar (2×10$^8$ Pa) or more may exist.

Two non-limiting examples of such high pressure fuel systems are: the common rail injection system, in which the fuel is compressed utilizing a high-pressure pump that supplies it to the fuel injection valves through a common rail; and the unit injection system which integrates the high-pressure pump and fuel injection valve in one assembly, achieving the highest possible injection pressures exceeding 2000 bar ($2 \times 10^8$ Pa). In both systems, in pressurising the fuel, the fuel gets hot, often to temperatures around 100° C., or above.

In common rail systems, the fuel is stored at high pressure in the central accumulator rail or separate accumulators prior to being delivered to the injectors. Often, some of the heated fuel is returned to the low pressure side of the fuel system or returned to the fuel tank. In unit injection systems the fuel is compressed within the injector in order to generate the high injection pressures. This in turn increases the temperature of the fuel.

In both systems, fuel is present in the injector body prior to injection where it is heated further due to heat from the combustion chamber. The temperature of the fuel at the tip of the injector can be as high as 250-350° C.

Thus the fuel is stressed at pressures from 1350 bar ($1.35 \times 10^8$ Pa) to over 2000 bar ($2 \times 10^8$ Pa) and temperatures from around 100° C. to 350° C. prior to injection, sometimes being recirculated back within the fuel system thus increasing the time for which the fuel experiences these conditions.

A common problem with diesel engines is fouling of the injector, particularly the injector body, and the injector nozzle. Fouling may also occur in the fuel filter. Injector nozzle fouling occurs when the nozzle becomes blocked with deposits from the diesel fuel. Fouling of fuel filters may be related to the recirculation of fuel back to the fuel tank. Deposits increase with degradation of the fuel. Deposits may take the form of carbonaceous coke-like residues, lacquers or sticky or gum-like residues. Diesel fuels become more and more unstable the more they are heated, particularly if heated under pressure. Thus diesel engines having high pressure fuel systems may cause increased fuel degradation. In recent years the need to reduce emissions has led to the continual redesign of injection systems to help meet lower targets. This has led to increasingly complex injectors and lower tolerance to deposits.

The problem of injector fouling may occur when using any type of diesel fuels. However, some fuels may be particularly prone to cause fouling or fouling may occur more quickly when these fuels are used. For example, fuels containing biodiesel and those containing metallic species may lead to increased deposits.

When injectors become blocked or partially blocked, the delivery of fuel is less efficient and there is poor mixing of the fuel with the air. Over time this leads to a loss in power of the engine, increased exhaust emissions and poor fuel economy.

Deposits are known to occur in the spray channels of the injector, leading to reduced flow and power loss. As the size of the injector nozzle hole is reduced, the relative impact of deposit build up becomes more significant. Deposits are also known to occur at the injector tip. Here, they affect the fuel spray pattern and cause less effective combustion and associated higher emissions and increased fuel consumption.

In addition to these "external" injector deposits in the nozzle hole and at the injector tip which lead to reduced flow and power loss, deposits may occur within the injector body causing further problems. These deposits may be referred to as internal diesel injector deposits (or IDIDs). IDIDs occur inside the injector on the critical moving parts. They can hinder the movement of these parts affecting the timing and quantity of fuel injection. Since modern diesel engines operate under very precise conditions these deposits can have a significant impact on performance.

IDIDs cause a number of problems, including power loss and reduced fuel economy due to less than optimal fuel metering and combustion. Initially the user may experience cold start problems and/or rough engine running. These deposits can lead to more serious injector sticking. This occurs when the deposits stop parts of the injector from moving and thus the injector stops working. When several or all of the injectors stick the engine may fail completely.

It is known to add nitrogen-containing detergents to diesel fuel to reduce coking. Typical nitrogen-containing detergents include those formed by the reaction of a polyisobutylene-substituted succinic acid derivative with a polyalkylene polyamine. However, newer engines including finer injector nozzles are more sensitive and current diesel fuels may not be suitable for use with the new engines incorporating these smaller nozzle holes.

As mentioned above, the problem of injector fouling may be more likely to occur when using fuel compositions comprising metal species. Various metal species may be present in fuel compositions. This may be due to contamination of the fuel during manufacture, storage, transport or use or due to contamination of fuel additives. Metal species may also be added to fuels deliberately. For example transition metals are sometimes added as fuel borne catalysts, for example to improve the performance of diesel particulate filters.

The present inventors believe that problems of injector sticking occur when metal or ammonium species, particularly sodium species, react with carboxylic acid species in the fuel.

Sodium contamination of diesel fuel and the resultant formation of carboxylate salts is believed to be a major cause of injector sticking.

In preferred embodiments the diesel fuel compositions used in the present invention comprise sodium and/or calcium. Preferably they comprise sodium. The sodium and/or calcium is typically present in a total amount of from 0.01 to 50 ppm, preferably from 0.05 to 5 ppm preferably 0.1 to 2 ppm such as 0.1 to 1 ppm.

Other metal-containing species may also be present as a contaminant, for example through the corrosion of metal and metal oxide surfaces by acidic species present in the fuel or from lubricating oil. In use, fuels such as diesel fuels routinely come into contact with metal surfaces for example, in vehicle fuelling systems, fuel tanks, fuel transportation means etc. Typically, metal-containing contamination may comprise transition metals such as zinc, iron and copper; other group I or group II metals and other metals such as lead.

The presence of metal containing species may give rise to fuel filter deposits and/or external injector deposits including injector tip deposits and/or nozzle deposits.

In addition to metal-containing contamination which may be present in diesel fuels there are circumstances where metal-containing species may deliberately be added to the fuel. For example, as is known in the art, metal-containing fuel-borne catalyst species may be added to aid with the regeneration of particulate traps. The presence of such catalysts may also give rise to injector deposits when the fuels are used in diesel engines having high pressure fuel systems.

Metal-containing contamination, depending on its source, may be in the form of insoluble particulates or soluble compounds or complexes. Metal-containing fuel-borne catalysts are often soluble compounds or complexes or colloidal species.

In some embodiments, the diesel fuel may comprise metal-containing species comprising a fuel-borne catalyst. Preferably, the fuel borne catalyst comprises one or more metals selected from iron, cerium, platinum, manganese, Group I and Group II metals e.g., calcium and strontium. Most preferably the fuel borne catalyst comprises a metal selected from iron and cerium.

In some embodiments, the diesel fuel may comprise metal-containing species comprising zinc. Zinc may be present in an amount of from 0.01 to 50 ppm, preferably from 0.05 to 5 ppm, more preferably 0.1 to 1.5 ppm.

Typically, the total amount of all metal-containing species in the diesel fuel, expressed in terms of the total weight of metal in the species, is between 0.1 and 50 ppm by weight, for example between 0.1 and 20 ppm, preferably between 0.1 and 10 ppm by weight, based on the weight of the diesel fuel.

It is advantageous to provide a diesel fuel composition which prevents or reduces the occurrence of deposits in a diesel engine. Such deposits may include "external" injector deposits such as deposits in and around the nozzle hole and at the injector tip and "internal" injector deposits or IDIDs. Such fuel compositions may be considered to perform a "keep clean" function i.e. they prevent or inhibit fouling. It is also be desirable to provide a diesel fuel composition which would help clean up deposits of these types. Such a fuel composition which when combusted in a diesel engine removes deposits therefrom thus effecting the "clean-up" of an already fouled engine.

As with "keep clean" properties, "clean-up" of a fouled engine may provide significant advantages. For example, superior clean up may lead to an increase in power and/or an increase in fuel economy. In addition removal of deposits from an engine, in particular from injectors may lead to an increase in interval time before injector maintenance or replacement is necessary thus reducing maintenance costs.

Although for the reasons mentioned above deposits on injectors is a particular problem found in modern diesel engines with high pressure fuels systems, it is desirable to provide a diesel fuel composition which also provides effective detergency in older traditional diesel engines such that a single fuel supplied at the pumps can be used in engines of all types.

It is also desirable that fuel compositions reduce the fouling of vehicle fuel filters. It is useful to provide compositions that prevent or inhibit the occurrence of fuel filter deposits i.e, provide a "keep clean" function. It is useful to provide compositions that remove existing deposits from fuel filter deposits i.e. provide a "clean up" function. Compositions able to provide both of these functions are especially useful.

According to a sixth aspect of the present invention there is provided a method of improving the performance of an engine, the method comprising combusting in said engine a fuel composition comprising as an additive a quaternary ammonium compound of formula (X):

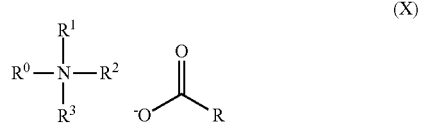

(X)

wherein $R^0$, $R^1$, $R^2$ and $R^3$ is each individually an optionally substituted alkyl, alkenyl and aryl group and R includes an optionally substituted hydrocarbyl moiety having at least 5 carbon atoms.

In preferred embodiments the sixth aspect of the present invention provides a method of improving the performance of an engine, the method comprising combusting in said engine a fuel composition comprising as an additive a quaternary ammonium compound which is the reaction product of:
(a) a tertiary amine;
(b) an acid-activated alkylating agent; and
(c) an acid including an optionally substituted alkyl or alkenyl moiety having at least 6 carbon atoms.

Preferred features of the sixth aspect of the present invention are as defined in relation to the first, second, third and fifth aspects.

The sixth aspect of the present invention may suitably provide a method of improving the performance of an engine comprising the steps of: preparing a quaternary additive according to the method of the second aspect; adding the quaternary ammonium salt additive to a fuel composition; and combusting the additised fuel composition in the engine.

Preferably the sixth aspect of the present invention comprises combusting in an engine a fuel composition comprising as an additive a quaternary ammonium compound which is the reaction product of:
(a) a tertiary amine;
(b) an epoxide; and
(c) an acid including an optionally substituted alkyl or alkenyl moiety having at least 5 carbon atoms, preferably at least 6 carbon atoms.

In the method of the sixth aspect the engine may be a gasoline engine and the fuel composition may be a gasoline fuel.

Preferably in the method of the sixth aspect the engine is a diesel engine and the fuel composition is a diesel fuel composition.

The method of the sixth aspect of the present invention is particularly effective at improving the performance of a modern diesel engine having a high pressure fuel system.

Such diesel engines may be characterised in a number of ways.

Such engines are typically equipped with fuel injection equipment meeting or exceeding "Euro 5" emissions legislation or equivalent legislation in US or other countries.

Such engines are typically equipped with fuel injectors having a plurality of apertures, each aperture having an inlet and an outlet.

Such engines may be characterised by apertures which are tapered such that the inlet diameter of the spray-holes is greater than the outlet diameter.

Such modern engines may be characterised by apertures having an outlet diameter of less than 500 μm, preferably less than 200 μm, more preferably less than 150 μm, preferably less than 100 μm, most preferably less than 80 μm or less.

Such modern diesel engines may be characterised by apertures where an inner edge of the inlet is rounded.

Such modern diesel engines may be characterised by the injector having more than one aperture, suitably more than 2 apertures, preferably more than 4 apertures, for example 6 or more apertures.

Such modern diesel engines may be characterised by an operating tip temperature in excess of 250° C.

Such modern diesel engines may be characterised by a a fuel injection system which provides a fuel pressure of more than 1350 bar, preferably more than 1500 bar, more preferably more than 2000 bar. Preferably, the diesel engine has fuel injection system which comprises a common rail injection system.

The method of the present invention preferably improves the performance of an engine having one or more of the above-described characteristics.

The method of the present invention improves the performance of an engine. This improvement in performance is suitably achieved by reducing deposits in the engine.

The present invention may therefore provide a method of combating deposits in an engine comprising combusting in said engine a fuel composition of the fourth aspect.

The sixth aspect of the present invention preferably relates to a method of combating deposits in an engine, preferably a diesel engine. Combating deposits may involve reducing or the preventing of the formation of deposits in an engine compared to when running the engine using unadditised fuel. Such a method may be regarded as achieving "keep clean" performance.

Combating deposits may involve the removal of existing deposits in an engine. This may be regarded as achieving "clean up" performance.

In especially preferred embodiments the method of the sixth aspect of the present invention may be used to provide "keep clean" and "clean up" performance.

As explained above deposits may occur at different places within a diesel engine, for example a modern diesel engine.

The present invention is particularly useful in the prevention or reduction or removal of internal deposits in injectors of engines operating at high pressures and temperatures in which fuel may be recirculated and which comprise a plurality of fine apertures through which the fuel is delivered to the engine. The present invention finds utility in engines for heavy duty vehicles and passenger vehicles. Passenger vehicles incorporating a high speed direct injection (or HSDI) engine may for example benefit from the present invention.

The present invention may also provide improved performance in modern diesel engines having a high pressure fuel system by controlling external injector deposits, for example those occurring in the injector nozzle and/or at the injector tip. The ability to provide control of internal injector deposits and external injector deposits is a useful advantage of the present invention.

Suitably the present invention may reduce or prevent the formation of external injector deposits. It may therefore provide "keep clean" performance in relation to external injector deposits.

Suitably the present invention may reduce or remove existing external injector deposits. It may therefore provide "clean up" performance in relation to external injector deposits.

Suitably the present invention may reduce or prevent the formation of internal diesel injector deposits. It may therefore provide "keep clean" performance in relation to internal diesel injector deposits.

Suitably the present invention may reduce or remove existing internal diesel injector deposits. It may therefore provide "clean up" performance in relation to internal diesel injector deposits.

The present invention may also combat deposits on vehicle fuel filters. This may include reducing or preventing the formation of deposits ("keep clean" performance) or the reduction or removal of existing deposits ("clean up" performance).

The diesel fuel compositions of the present invention may also provide improved performance when used with traditional diesel engines. Preferably the improved performance is achieved when using the diesel fuel compositions in modern diesel engines having high pressure fuel systems and when using the compositions in traditional diesel engines. This is important because it allows a single fuel to be provided that can be used in new engines and older vehicles.

The removal or reduction of IDIDs according to the present invention will lead to an improvement in performance of the engine.

The improvement in performance of the diesel engine system may be measured by a number of ways. Suitable methods will depend on the type of engine and whether "keep clean" and/or "clean up" performance is measured.

An improvement in "keep clean" performance may be measured by comparison with a base fuel. "Clean up" performance can be observed by an improvement in performance of an already fouled engine.

The effectiveness of fuel additives is often assessed using a controlled engine test.

In Europe the Co-ordinating European Council for the development of performance tests for transportation fuels, lubricants and other fluids (the industry body known as CEC), has developed a test for additives for modern diesel engines such as HSDI engines. The CEC F-98-08 test is used to assess whether diesel fuel is suitable for use in engines meeting new European Union emissions regulations known as the "Euro 5" regulations. The test is based on a Peugeot DW10 engine using Euro 5 injectors, and is commonly referred to as DW10 test. This test measures power loss in the engine due to deposits on the injectors, and is further described in example 6.

According to a seventh aspect of the present invention there the use of an additive in a fuel composition to improve the performance of an engine combusting said fuel composition wherein the additive is a quaternary ammonium compound of formula (X):

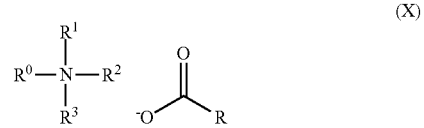

wherein $R^0$, $R^1$, $R^2$ and $R^3$ is each individually an optionally substituted alkyl, alkenyl and aryl group and R includes an optionally substituted hydrocarbyl moiety having at least 5 carbon atoms.

According to a seventh aspect of the present invention there the use of an additive in a fuel composition to improve the performance of an engine combusting said fuel composition wherein the additive is a quaternary ammonium compound which is the reaction product of:
  (a) a tertiary amine;
  (b) an acid-activated alkylating agent; and
  (c) an acid including an optionally substituted alkyl or alkenyl moiety having at least 5 carbon atoms, preferably at least 6 carbon atoms.

Preferred features of the seventh aspect of the present invention are as defined in relation to the first, second, third and fifth aspects, and especially as defined in relation to the sixth aspect.

BRIEF DESCRIPTION OF THE DRAWING

FIG. 1 is a graph of observed power change versus time for fuel compositions 1-3 tested according to the CECF-98-08 DW 10 method.

The invention will now be further described with reference to the following non-limiting examples. In the examples which follow the values given in parts per million (ppm) for treat rates denote active agent amount, not the amount of a formulation as added, and containing an active agent. All parts per million are by weight.

EXAMPLE 1

Additive A1 was prepared as follows.

A sample of polyisobutenyl succinic anhydride prepared from 1000 MW pib (PIB1000SA) was hydrolysed by reaction with a slight excess of water at 90-95° C. The acid value of the resulting PIB1000SAcid was determined to be 1.50 mmol/g by titration against 0.1 N lithium methoxide in toluene.

The PIB1000SAcid sample (50.10 g, 75 mmol CO2H) was charged to a 3-neck round bottom flask. The flask was fitted with $N_2$ flush, reflux condenser, stirrer-bar and thermocouple well. An oil bath thermostatically controlled to maintain 105° C. was used to heat the flask contents with stirrin. The flask was charged with Shellsol AB (70.73 g) and was heated with strong stirring to 95° C. Water (3.384 g, 188 mmol, 2.51 equivalents to CO2H) was added forming a turbid solution.

N,N-Dimethyl ethanolamine (6.76 g, 76 mmol, 1.0 equivalents) was then added. This significantly reduced but did not remove the turbidity. FTIR confirmed the formation of an amine salt. After a further two hours a second FTIR spectrum was essentially unchanged from the first.

2-ethylhexylglycidyl ether (14.06 g, 75.6 mmol, 1.01 equivalents) was added, dropping the temperature from 94 to 88° C. Heating continued and after a further 90 minutes at a temperature of 95° C. a further FTIR spectrum was acquired. The peak associated with the carboxylate salt had shifted slightly to 1574 cm-1 and approximately doubled in height relative to the $CH_2$ absorbances at 1463 and 1455 cm-1. Additive A1, the di-quaternary ammonium salt of PIB1000SAcid via the ring-opening of 2-ethylhexylglycidyl ether with N,N-dimethyl ethanolamine was formed as a 50% solution in aromatic solvent.

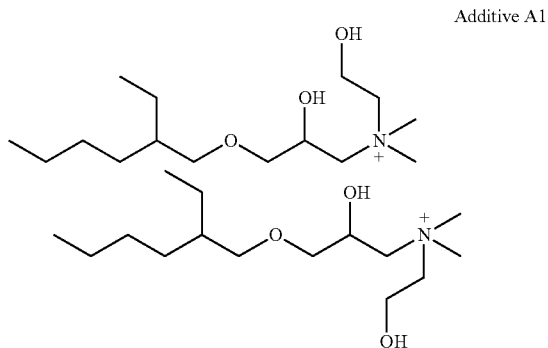

Additive A1

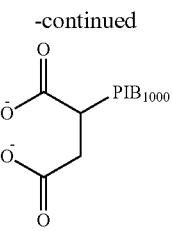

-continued

EXAMPLE 2

Further compounds of the invention and comparative compounds were prepared using a method analogous to example 1 except that the acid was replaced by an acid having the formula $HOOCCHRCH_2COOH$, as follows:

| Compound | R |
| --- | --- |
| A2 | 750 MW PIB |
| A3 | 440 MW PIB |
| A4 | 260 MW PIB |
| A5 | n-C18 |
| A6 | n-C12 |
| A7 (comparative) | H |

In each case the same amine and epoxide as example 1 were used.

EXAMPLE 3

Additive A8 was prepared as follows.

A 100 cm³ 3-neck round-bottom flask was charged with PIB1000SA (19.73 g, 15.4 mmol of anhydride by LiOMe titration) and 2-ethylhexanol (2.008 g, 15.4 mmol, 1.008 equivalents).

The flask was fitted with N2 flush, reflux condenser, stirrer-bar and thermocouple well. An oil bath thermostatically controlled to maintain 105° C. was used to heat the flask contents with stirring to 83° C. The temperature of the oil bath thermostat was re-set to 110° C. Reaction monitoring by FTIR confirmed that the reaction was substantially complete and a half-ester, half-acid formed after one hour. A further aliquot of 2-ethylhexanol (0.204 g, 0.1 equivalents) was added and FTIR used to confirm that no further reaction had occurred after a further 40 minutes.

A previously prepared sample of PIB1000SI-DMAPA (reaction product of PIB1000SA with N,N-dimethyl propylamine, 21.18 g, 15.5 mmol, 1.01 equivalents) and 2-methylphenylglycidyl ether, 2.526 g, 15.4 mmol, 1.0 equivalents) were added to the reaction flask. FTIR monitoring showed that a peak at about 1589 cm-1, consistent with formation of a carboxylate salt, began to form immediately. After 3 hours the peak had doubled in intensity and shifted to 1573 cm-1. No further changes were noted on further heating.

The material was allowed to cool then warmed back to 60° C. before adding Caromax 20 solvent (45.52 g for a total 50.2% inactives) to the highly viscous material. A homogeneous mixture was formed comprising Additive A2 as a 50% solution in aromatic solvent.

Additive A8

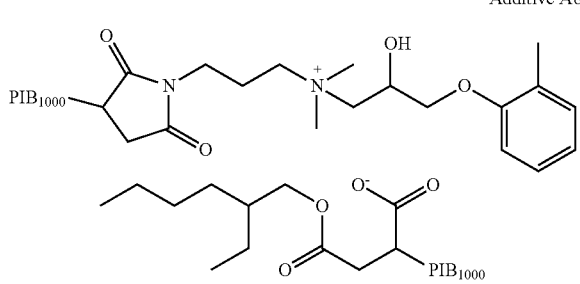

EXAMPLE 4

Additive A9 of the invention was prepared using a method analogous to that described in example 1. In this case 2 molar equivalents of dimethylethanolamine were reacted with 2 molar equivalents of dodecylene oxide and one equivalent of dodecenyl succinic acid.

EXAMPLE 5

Comparative

Additive A10 (not of the invention) was prepared from dimethylethanolamine, 2-ethylhexyl glycidyl ether and acetic acid

EXAMPLE 6

Comparative

Additive B is a 60% active ingredient solution (in aromatic solvent) of a polyisobutenyl succinimide obtained from the condensation reaction of a polyisobutenyl succinic anhydride derived from polyisobutene of Mn approximately 750 with a polyethylene polyamine mixture of average composition approximating to tetraethylene pentamine. The product was obtained by mixing the PIBSA and polyethylene polyamine at 50° C. under nitrogen and heating at 160° C. for 5 hours with removal of water.

EXAMPLE 7

Comparative

Additive C

A reactor was charged with 33.2 kg (26.5 mol) PIBSA (made from 1000 MW PIB and maleic anhydride) and heated to 90° C. DMAPA (2.71 kg, 26.5 mol) was charged and the mixture stirred for 1 hour at 90-100° C. The temperature was increased to 140° C. for 3 hours and water removed. Methyl salicylate (4.04 kg, 26.5 mol) was charged and the mixture held at 140° C. for 8 hours. Caromax 20 (26.6 kg) was added.

EXAMPLE 8

Diesel fuel compositions were prepared comprising the additives listed in Table 1, added to aliquots all drawn from a common batch of RF06 base fuel, and containing 1 ppm zinc (as zinc neodecanoate).

TABLE 1

| Fuel Composition | Additive | (ppm active) |
|---|---|---|
| 1 | A1 | 50 |
| 2 | B | 60 |
| 3 | C | 60 |

Table 2 below shows the specification for RF06 base fuel.

TABLE 2

| Property | Units | Limits Min | Limits Max | Method |
|---|---|---|---|---|
| Cetane Number | | 52.0 | 54.0 | EN ISO 5165 |
| Density at 15° C. | kg/m$^3$ | 833 | 837 | EN ISO 3675 |
| Distillation | | | | |
| 50% v/v Point | ° C. | 245 | — | |
| 95% v/v Point | ° C. | 345 | 350 | |
| FBP | ° C. | — | 370 | |
| Flash Point | ° C. | 55 | — | EN 22719 |
| Cold Filter Plugging Point | ° C. | — | −5 | EN 116 |
| Viscosity at 40° C. | mm$^2$/sec | 2.3 | 3.3 | EN ISO 3104 |
| Polycyclic Aromatic Hydrocarbons | % m/m | 3.0 | 6.0 | IP 391 |
| Sulphur Content | mg/kg | — | 10 | ASTM D 5453 |
| Copper Corrosion | | — | 1 | EN ISO 2160 |
| Conradson Carbon Residue on 10% Dist. Residue | % m/m | — | 0.2 | EN ISO 10370 |
| Ash Content | % m/m | — | 0.01 | EN ISO 6245 |
| Water Content | % m/m | — | 0.02 | EN ISO 12937 |
| Neutralisation (Strong Acid) Number | mg KOH/g | — | 0.02 | ASTM D 974 |
| Oxidation Stability | mg/mL | — | 0.025 | EN ISO 12205 |
| HFRR (WSD1,4) | μm | — | 400 | CEC F-06-A-96 |
| Fatty Acid Methyl Ester | | | prohibited | |

EXAMPLE 9

Fuel compositions 1 to 3 listed in table 1 were tested according to the CECF-98-08 DW 10 method.

The engine of the injector fouling test is the PSA DW10BTED4. In summary, the engine characteristics are:

Design: Four cylinders in line, overhead camshaft, turbocharged with EGR

Capacity: 1998 cm$^3$

Combustion chamber: Four valves, bowl in piston, wall guided direct injection

Power: 100 kW at 4000 rpm

Torque: 320 Nm at 2000 rpm

Injection system: Common rail with piezo electronically controlled 6-hole injectors.

Max. pressure: 1600 bar (1.6×10$^8$ Pa). Proprietary design by SIEMENS VDO

Emissions control: Conforms with Euro IV limit values when combined with exhaust gas post-treatment system (DPF)

This engine was chosen as a design representative of the modern European high-speed direct injection diesel engine capable of conforming to present and future European emissions requirements. The common rail injection system uses a highly efficient nozzle design with rounded inlet edges and conical spray holes for optimal hydraulic flow. This type of nozzle, when combined with high fuel pressure has allowed advances to be achieved in combustion efficiency, reduced noise and reduced fuel consumption, but are sensitive to influences that can disturb the fuel flow, such as deposit formation in the spray holes. The presence of these deposits causes a significant loss of engine power and increased raw emissions.

The test is run with a future injector design representative of anticipated Euro V injector technology.

It is considered necessary to establish a reliable baseline of injector condition before beginning fouling tests, so a sixteen hour running-in schedule for the test injectors is specified, using non-fouling reference fuel.

Full details of the CEC F-98-08 test method can be obtained from the CEC. The coking cycle is summarised below.

1. A warm up cycle (12 minutes) according to the following regime:

| Step | Duration (minutes) | Engine Speed (rpm) | Torque (Nm) |
|---|---|---|---|
| 1 | 2 | idle | <5 |
| 2 | 3 | 2000 | 50 |
| 3 | 4 | 3500 | 75 |
| 4 | 3 | 4000 | 100 |

2. 8 hrs of engine operation consisting of 8 repeats of the following cycle

| Step | Duration (minutes) | Engine Speed (rpm) | Load (%) | Torque (Nm) | Boost Air After IC (° C.) |
|---|---|---|---|---|---|
| 1 | 2 | 1750 | (20) | 62 | 45 |
| 2 | 7 | 3000 | (60) | 173 | 50 |
| 3 | 2 | 1750 | (20) | 62 | 45 |
| 4 | 7 | 3500 | (80) | 212 | 50 |
| 5 | 2 | 1750 | (20) | 62 | 45 |
| 6 | 10 | 4000 | 100 | * | 50 |
| 7 | 2 | 1250 | (10) | 20 | 43 |
| 8 | 7 | 3000 | 100 | * | 50 |
| 9 | 2 | 1250 | (10) | 20 | 43 |
| 10 | 10 | 2000 | 100 | * | 50 |
| 11 | 2 | 1250 | (10) | 20 | 43 |
| 12 | 7 | 4000 | 100 | * | 50 |

* for expected range see CEC method CEC-F-98-08

3. Cool down to idle in 60 seconds and idle for 10 seconds
4. 4 hrs soak period

The standard CEC F-98-08 test method consists of 32 hours engine operation corresponding to 4 repeats of steps 1-3 above, and 3 repeats of step 4, i.e. 56 hours total test time excluding warm ups and cool downs.

The results of these tests are shown in FIG. 1.

EXAMPLE 10

The effectiveness of the additives detailed in table 3 below in older engine types was assessed using a standard industry test—CEC test method No. CEC F-23-A-01.

This test measures injector nozzle coking using a Peugeot XUD9 A/L Engine and provides a means of discriminating between fuels of different injector nozzle coking propensity. Nozzle coking is the result of carbon deposits forming between the injector needle and the needle seat. Deposition of the carbon deposit is due to exposure of the injector needle and seat to combustion gases, potentially causing undesirable variations in engine performance.

The Peugeot XUD9 A/L engine is a 4 cylinder indirect injection Diesel engine of 1.9 liter swept volume, obtained from Peugeot Citroen Motors specifically for the CEC PF023 method.

The test engine is fitted with cleaned injectors utilising unflatted injector needles. The airflow at various needle lift positions have been measured on a flow rig prior to test. The engine is operated for a period of 10 hours under cyclic conditions.

| Stage | Time (secs) | Speed (rpm) | Torque (Nm) |
|---|---|---|---|
| 1 | 30 | 1200 ± 30 | 10 ± 2 |
| 2 | 60 | 3000 ± 30 | 50 ± 2 |
| 3 | 60 | 1300 ± 30 | 35 ± 2 |
| 4 | 120 | 1850 ± 30 | 50 ± 2 |

The propensity of the fuel to promote deposit formation on the fuel injectors is determined by measuring the injector nozzle airflow again at the end of test, and comparing these values to those before test. The results are expressed in terms of percentage airflow reduction at various needle lift positions for all nozzles. The average value of the airflow reduction at 0.1 mm needle lift of all four nozzles is deemed the level of injector coking for a given fuel.

The results of this test using the specified additive combinations of the invention are shown in table 3. In each case the specified amount of additive was added to an RF06 base fuel meeting the specification given in table 2 (example 8) above.

TABLE 3

| Composition | Additive (ppm active) | XUD-9 % Average Flow Loss |
|---|---|---|
|  | None | 69.0 |
| 4 | A1 (50) | 1.8 |
| 5 | A2 (50) | 2.0 |
| 7 | A3 (50) | 4.0 |
| 8 | A4 (50) | 13.0 |
| 9 | A5 (50) | 2.8 |
| 10 | A6 (50) | 1.3 |
| 11 (comparative) | A7 (50) | 45.6 |
| 12 | A8 (50) | 6.3 |
| 13 | A9 (50) | 5.6 |
| 14 (comparative) | A10 (50) | 40.8 |
| 15 (comparative) | B (60) | 25.5 |

These results show that the quaternary ammonium salt additives of the present invention achieve an excellent reduction in the occurrence of deposits in traditional diesel engines.

EXAMPLE 11

Additive A11, a further additive of the invention was prepared as follows:

With FTIR monitoring, a sample of technical grade oleic acid (Fisher, 15.31 g) was caused to mix with iso-propyl-glycidyl ether (6.36 g) by magnetic stirring before addition of water (3.90 g) and finally N,N-dimethyl ethanolamine (14.45 g). Amine addition was accompanied by a temperature rise from 21 to 30° C., controlled by raising up an oil bath at ambient temperature around the flask. After the initial exotherm had died down, the oil bath heater was turned on and set to provide 100° C. After three hours at an internal temperature of 94-95° C. the reaction was adjudged, by FTIR, to be complete. The reaction mass was transferred to a pear-shaped flask and stripped at the rotary evaporator at 100° C., 9 mBar. Mass balances were consistent with formation of the desired 2-hydroxy-N-(2-hydroxyethyl)-3- isopropoxy-N,N-dimethylpropan-1-aminium salt of oleic acid. A trace of ester was apparent in the IR spectra.

The invention claimed is:

1. A fuel composition comprising as an additive one or more quaternary ammonium compounds of formula (X):

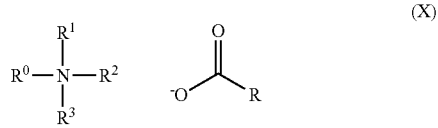

(X)

wherein $R^0$, $R^1$, $R^2$ and $R^3$ is each individually an optionally substituted alkyl, alkenyl or aryl group and R is an optionally substituted C10 to C36 alkyl or alkenyl group, wherein $RCOO^{31}$ is the residue of a monoacid and $R^0$ is the residue of an epoxide selected from the group consisting of: styrene oxide, ethylene oxide, propylene oxide, butylene oxide, epoxyhexane, octane oxide and stilbene oxide, and glycidyl ethers and glycidyl esters.

2. The fuel composition according to claim 1 wherein the fuel is diesel fuel.

3. The fuel composition according to claim 2 further comprising one or more detergents selected from the group consisting of:
   (i) an additional quaternary ammonium salt additive which is not one of the one or more quaternary ammonium compounds of claim 1;
   (ii) the product of a Mannich reaction between an aldehyde, an amine and an optionally substituted phenol;
   (iii) the reaction product of a carboxylic acid-derived acylating agent and an amine;
   (iv) the reaction product of a carboxylic acid-derived acylating agent and hydrazine;
   (v) a salt formed by the reaction of a carboxylic acid with di-n-butylamine or tri-n-butylamine;
   (vi) the reaction product of a hydrocarbyl-substituted dicarboxylic acid or anhydride and an amine compound or salt which product comprises at least one amino triazole group; and
   (vii) a substituted polyaromatic detergent additive.

4. The fuel composition according to claim 1 wherein the fuel is gasoline fuel.

5. The fuel composition according to claim 4 which further comprises one or more gasoline detergents selected from the group consisting of:
   (p) hydrocarbyl-substituted polyoxyalkylene amines or polyetheramines;
   (q) acylated nitrogen compounds which are the reaction product of a carboxylic acid-derived acylating agent and an amine;
   (r) hydrocarbyl-substituted amines wherein the hydrocarbyl substituent is substantially aliphatic and contains at least 8 carbon atoms;
   (s) Mannich base additives comprising nitrogen-containing condensates of a phenol, aldehyde and primary or secondary amine;
   (t) aromatic esters of a polyalkylphenoxyalkanol;
   (u) an additional quaternary ammonium salt additive which is not a quaternary ammonium compound of claim 1; and
   (v) tertiary hydrocarbyl amines having a maximum of 30 carbon atoms.

6. A method of improving the performance of an engine, the method comprising combusting in said engine a fuel composition comprising as an additive one or more quaternary ammonium compounds of formula (X):

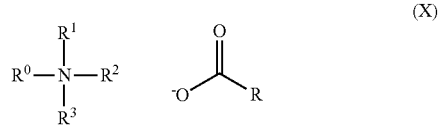

(X)

wherein $R^0$, $R^1$, $R^2$ and $R^3$ is each individually an optionally substituted alkyl, alkenyl or aryl group and R is an optionally substituted C10 to C36 alkyl or alkenyl group, wherein $RCOO^{31}$ is the residue of a monoacid and $R^0$ is the residue of an epoxide selected from the group consisting of: styrene oxide, ethylene oxide, propylene oxide, butylene oxide, epoxyhexane, octane oxide and stilbene oxide; and glycidyl ethers and glycidyl esters.

7. The method according to claim 6 wherein the engine is a gasoline engine and the fuel is gasoline.

8. The method according to claim 6 wherein the engine is a diesel engine having a fuel injection system which comprises a high pressure fuel injection (HPFI) system with fuel pressures greater than 1350 bar.

9. The method according to claim 6 wherein improvement in performance is achieved by combating deposits in the engine.

10. The method according to claim 9 which combats internal diesel injector deposits.

11. The method according to claim 9 which combats external diesel injector deposits, including injector nozzle deposits and injector tip deposits.

12. The method according to claim 7 which combats fuel filter deposits.

13. The fuel composition according to claim 1 wherein the glycidyl ethers or glycidyl esters are selected from the group consisting of glycidyl 2 methyl phenyl ether and glycidyl ester of versatic acid.

14. The method according to claim 6 wherein the glycidyl ethers or glycidyl esters are selected from the group consisting of glycidyl 2 methyl phenyl ether and glycidyl ester of versatic acid.

* * * * *

UNITED STATES PATENT AND TRADEMARK OFFICE
CERTIFICATE OF CORRECTION

PATENT NO. : 10,351,791 B2
APPLICATION NO. : 14/907693
DATED : July 16, 2019
INVENTOR(S) : Jacqueline Reid and Stephen L. Cook Page 1 of 1

It is certified that error appears in the above-identified patent and that said Letters Patent is hereby corrected as shown below:

In the Claims

In Column 41, Line 17 (Claim 1), "RCOO31" should read -- RCOO- --

In Column 42, Line 26 (Claim 6), "RCOO31" should read -- RCOO- --

Signed and Sealed this
Seventeenth Day of September, 2019

Andrei Iancu
*Director of the United States Patent and Trademark Office*